(12) United States Patent
Tan et al.

(10) Patent No.: US 12,153,061 B2
(45) Date of Patent: *Nov. 26, 2024

(54) CARTRIDGE ASSEMBLY TRAY FOR IMMUNOASSAY TESTS

(71) Applicant: Access Medical Systems, LTD., Palo Alto, CA (US)

(72) Inventors: Hong Tan, San Jose, CA (US); Yongli Ren, Shanghai (CN); Ming Xia, Shanghai (CN); Genqian Li, Shanghai (CN)

(73) Assignee: ACCESS MEDICAL SYSTEMS, LTD., Palo Alto, CA (US)

( * ) Notice: Subject to any disclaimer, the term of this patent is extended or adjusted under 35 U.S.C. 154(b) by 928 days.

This patent is subject to a terminal disclaimer.

(21) Appl. No.: 17/181,868

(22) Filed: Feb. 22, 2021

(65) Prior Publication Data

US 2021/0172970 A1 Jun. 10, 2021

Related U.S. Application Data

(63) Continuation of application No. 16/217,730, filed on Dec. 12, 2018, now Pat. No. 10,928,406, which is a
(Continued)

(51) Int. Cl.
*B01L 9/00* (2006.01)
*B01L 3/00* (2006.01)
(Continued)

(52) U.S. Cl.
CPC .... *G01N 35/00029* (2013.01); *B01L 3/50855* (2013.01); *B01L 9/52* (2013.01);
(Continued)

(58) Field of Classification Search
CPC .... B01L 9/06; B01L 9/065; B01L 9/50; B01L 9/52; B01L 9/523; G01N 30/025;
(Continued)

(56) References Cited

U.S. PATENT DOCUMENTS

| 5,167,922 A | 12/1992 | Long |
| 6,190,619 B1 | 2/2001 | Kilcoin et al. |

(Continued)

FOREIGN PATENT DOCUMENTS

| EP | 2336746 A2 | 6/2011 |
| WO | 199747388 A1 | 12/1997 |

(Continued)

OTHER PUBLICATIONS

International Search Report and Written Opinion of PCT Application No. PCT/US2014/059264, mailed Jan. 20, 2015.

(Continued)

*Primary Examiner* — Jill A Warden
*Assistant Examiner* — Dwayne K Handy
(74) *Attorney, Agent, or Firm* — Perkins Coie LLP; Viola T. Kung; Andrew T. Pettit

(57) ABSTRACT

This invention relates to a cartridge assembly tray for conducting automated biochemical tests, such as immunoassay tests. The tray comprises a base member, a hinged frame and a locking mechanism. The base member includes a plurality of slots within the base member. Each of the plurality of slots is to receive a test cartridge. The hinged frame is coupled to the base member. The hinged frame is capable to rotate to an opened position or a closed position. The hinged frame includes a horizontal push bar configured to apply a downward force to test cartridges received in the plurality of slots when the hinged frame is in the closed position. The locking mechanism is to lock the hinged frame in the closed position when the hinged frame rotates to the closed position.

15 Claims, 23 Drawing Sheets

Related U.S. Application Data continuation of application No. 15/475,998, filed on Mar. 31, 2017, now Pat. No. 10,161,945, which is a continuation of application No. 15/089,812, filed on Apr. 4, 2016, now Pat. No. 9,616,427, which is a continuation of application No. PCT/US2014/059264, filed on Oct. 6, 2014.

(60) Provisional application No. 61/887,842, filed on Oct. 7, 2013.

(51) Int. Cl.
| | |
|---|---|
| *G01N 33/53* | (2006.01) |
| *G01N 33/536* | (2006.01) |
| *G01N 35/00* | (2006.01) |
| *G01N 35/04* | (2006.01) |

(52) U.S. Cl.
CPC .......... *B01L 9/527* (2013.01); *G01N 33/5304* (2013.01); *G01N 33/536* (2013.01); *B01L 2200/025* (2013.01); *B01L 2200/04* (2013.01); *B01L 2300/043* (2013.01); *B01L 2300/0609* (2013.01); *B01L 2300/0809* (2013.01); *G01N 2035/00148* (2013.01); *G01N 2035/0418* (2013.01); *G01N 2035/0436* (2013.01)

(58) Field of Classification Search
CPC .. G01N 30/026; G01N 30/028; G01N 35/025; G01N 35/026; G01N 35/028; G01N 35/00029

See application file for complete search history.

(56) References Cited

U.S. PATENT DOCUMENTS

| | | |
|---|---|---|
| 7,131,166 B2 | 11/2006 | Cohen et al. |
| 8,361,387 B2 | 1/2013 | Schacher et al. |
| 9,616,427 B2 | 4/2017 | Tan et al. |
| 10,161,945 B2 | 12/2018 | Tan et al. |
| 10,928,406 B2 * | 2/2021 | Tan ...................... G01N 33/536 |
| 2009/0136386 A1 | 5/2009 | Duffy et al. |
| 2010/0132484 A1 | 6/2010 | Schacher et al. |
| 2011/0253650 A1 * | 10/2011 | Renz ...................... A47L 15/503 |
| | | 211/41.9 |
| 2012/0051987 A1 | 3/2012 | Johnson et al. |

FOREIGN PATENT DOCUMENTS

| | | |
|---|---|---|
| WO | 0174091 A2 | 10/2001 |
| WO | 2012066499 A1 | 5/2012 |
| WO | 2012094625 A2 | 7/2012 |

OTHER PUBLICATIONS

Supplementary European Search Report dated May 11, 2017 of EPO Application No. 14852101.6.

* cited by examiner

CARTRIDGE ASSEMBLY TRAY FOR IMMUNOASSAY TESTS

This application is a continuation of U.S. application Ser. No. 16/217,730, filed Dec. 12, 2018, which is a continuation of U.S. application Ser. No. 15/475,998, filed Mar. 31, 2017, now U.S. Pat. No. 10,161,945, issued Dec. 25, 2018, which is a continuation of U.S. application Ser. No. 15/089,812, filed Apr. 4, 2016, now U.S. Pat. No. 9,616,427, issued Apr. 11, 2017; which is a continuation of PCT/US2014/059264, filed Oct. 6, 2014; which claims the benefit of U.S. Provisional Application No. 61/887,842, filed Oct. 7, 2013. The contents of the above-identified applications are incorporated herein by reference in their entirety.

FIELD OF THE INVENTION

This invention relates to a cartridge assembly tray for conducting automated immunoassay tests. The cartridge assembly tray secures test cartridges into an assembly to be inserted to an immunoassay apparatus for conducting the test.

BACKGROUND OF THE INVENTION

In the development of immunoassay systems, many performance requirements need be met. Assays need be sensitive enough to detect analyte at very low levels in the subpicogram to nanogram per milliliter range. Total assay time needs to be 15 minutes or less in order to provide timely results for patient management in point of care situations, or to meet throughput requirements for batch analyzers. In some cases, analyte panels where multiple assays are simultaneously performed with the same sample are advantageous in order to minimize the turnaround time for results and test costs. All-in-one reagent cartridge and an automatic system conducting an immunoassay test on the cartridge is desired for minimal human input error, cost saving, and prompt results.

Since the cartridges are disposable items, it is necessary to replace the cartridge from time to time between the tests. For conventional immunoassay systems, operators of the systems need to manually insert the individual cartridges into the systems. Such a process takes time and is prone to human errors.

SUMMARY OF THE INVENTION

The present invention is directed to a cartridge assembly tray for conducting automated immunoassay tests. The tray comprises a base member, a hinged frame coupled to the base member, and a locking mechanism. The base member includes a plurality of slots within the base member. Each of the plurality of slots is to receive a test cartridge. The hinged frame is capable to rotate to an opened position or a closed position. The hinged frame including a horizontal push bar configured to apply a downward force to test cartridges received in the plurality of slots when the hinged frame is in the closed position. The locking mechanism is configured to lock the hinged frame in the closed position when the hinged frame rotates to the closed position.

The present invention is also directed to a method for loading a plurality of test cartridges into a test apparatus. The method comprises obtaining the tray; loading the test cartridges into the slots of the base member, wherein the slots fit the test cartridges to prevent the test cartridges from moving laterally in the slots; rotating the hinged frame of the tray to the closed position, wherein the horizontal push bar applies the downward force to the test cartridges secured in the slots when the hinged frame is in the closed position; locking the hinged frame to the closed position by the locking mechanism of the tray; and inserting the tray into a test apparatus.

The present invention is also directed to a method for performing a biochemical test in the test cartridges. The method comprises loading the test cartridges into the test apparatus; opening the cap of each of the test cartridges; lifting the probe from the test cartridge; and dipping the probe into the sample well, the reagent wells, the wash wells and the measurement well of the individual test cartridge in a predetermined sequence.

DETAILED DESCRIPTION OF THE INVENTION

Definitions

Terms used in the claims and specification are to be construed in accordance with their usual meaning as understood by one skilled in the art except and as defined as set forth below.

"About," as used herein, refers to within ±10% of the recited value.

An "analyte-binding" molecule, as used herein, refers to any molecule capable of participating in a specific binding reaction with an analyte molecule. Examples include but are not limited to, (i) antigen molecules, for use in detecting the presence of antibodies specific against that antigen; (ii) antibody molecules, for use in detecting the presence of antigens; (iii) protein molecules, for use in detecting the presence of a binding partner for that protein; (iv) ligands, for use in detecting the presence of a binding partner; or (v) single stranded nucleic acid molecules, for detecting the presence of nucleic acid binding molecules.

A "binding pair," as used herein, refers to two molecules that are attracted to each other and specifically bind to each other. Examples of binding pairs include, but not limited to, an antigen and an antibody against the antigen, a ligand and its receptor, complementary strands of nucleic acids, biotin and avidin, biotin and streptavidin, lectin and carbohydrates. Preferred binding pairs are biotin and streptavidin, biotin and avidin, fluorescein and anti-fluorescein, digioxigenin/anti-digioxigenin. Biotin and avidin, including biotin derivatives and avidin derivatives such as streptavidin, may be used as intermediate binding substances in assay protocols employing complex binding sequences. For example, antibodies may be labeled with biotin ("biotinylated") and used to bind to a target substance previously immobilized on a solid phase surface. Fluorescent compositions according to the present invention employing an avidin or streptavidin may then be used to introduce the fluorescent label.

"Immobilized," as used herein, refers to reagents being fixed to a solid surface. When a reagent is immobilized to a solid surface, it is either be non-covalently bound or covalently bound to the surface.

A "probe," as used herein, refers to a substrate coated with analyte-binding molecules at the sensing (detecting) side. A probe has a bottom tip. The bottom tip has a sensing surface coated with analyte-binding molecules.

Cartridge Tray

Figure 1:
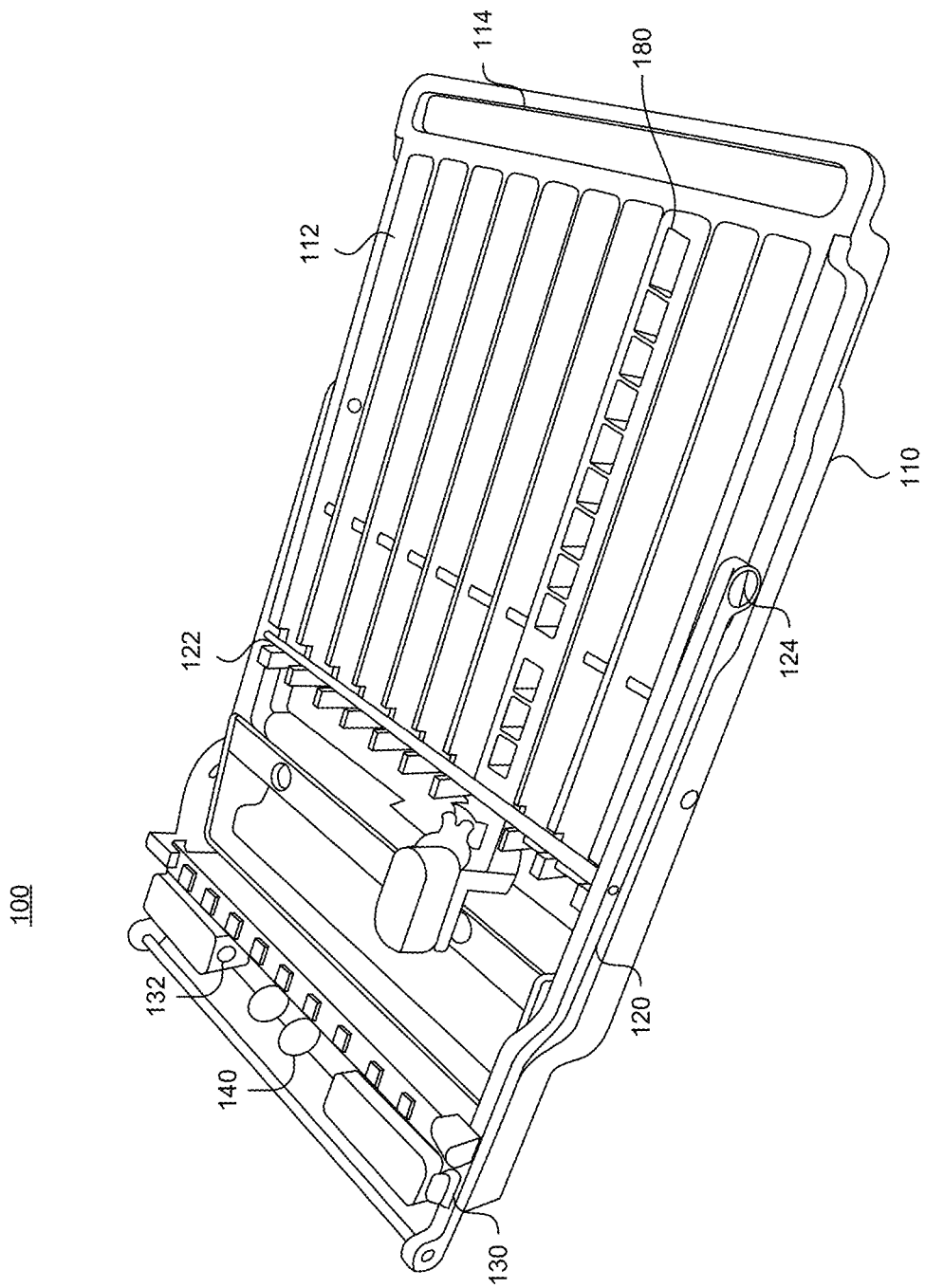
FIG. 1 illustrates an example of a cartridge tray in a closed position to be used in a biochemical test.

Referring now to the drawings, and particularly to FIG. 1, there is shown a cartridge tray of the present invention, which generally can carry one or more test cartridges. The cartridge tray can carry preferably 2~16 test cartridges, more preferably 4~10 cartridges. During operation of a test apparatus, the test apparatus moves the cartridge tray 100 into the apparatus to position the cartridge tray 100 as necessary for the apparatus to drop test probe at precise locations in the wells of the test cartridges secured in the cartridge tray 100. In the embodiment shown in FIG. 1, the cartridge tray 100 includes a base member 110, a hinged frame 120 and a locking mechanism 130.

The base member 110 includes a plurality of slots 112 within the base member 129. Each of the plurality of slots 112 is to receive a test cartridge 180. As shown in FIG. 1, each of the plurality of slots 112 has a top opening for receiving a test cartridge 180. The slot 112 has a size (e.g., length and width) to fit a test cartridge 180 and to prevent the test cartridge 180 from moving laterally in the slot 112. The slots 112 can have shapes consistent with the outer shapes of the test cartridge 180. For instance, each of the plurality of slots 112 can have a substantially rectangular shape for receiving a test cartridge 180, while the test cartridge 180 has a substantially rectangular outer shape. Each of the slots 112 has at least one opening at the bottoms of the slots 112 such that optical signals from the test cartridge 100 is capable to be collected from bottoms of the slots 112. In some embodiments, the bottoms of the slots 112 are not covered so that the tray 100 can have less weight.

The base member 110 can have outside surfaces that include grooves adapted to guide the tray into a tray drive of a test apparatus. In other words, the base member includes the grooves on both sides of the base member. The sides are defined as the side surfaces that are parallel to the axis of the slots of the base member 110. For instance, the grooves can be arranged in parallel with an axis of the tray 100. The grooves guide the tray 100 into a test apparatus when a user inserts the tray 100 into the test apparatus. The cartridge tray 100 can further include a handle 114 attached to the base member 110 such that a test apparatus can grip the handle 114 and move the tray 100 into a tray drive of the test apparatus. Alternatively, the handle 114 can be used by a user to push the tray 100 into a test apparatus.

The hinged frame 120 is coupled to the base member 110 via one or more hinge 124. For instance, the hinge 124 can be a bearing that connects the base member 110 and the hinged frame 120, allowing only a limited angle of rotation between the base member 110 and the hinged frame 120. The hinge can be a barrel hinge, a pivot hinge, a butt hinge, a case hinge, a piano hinge, a concealed hinge, a butterfly hinge, a flag hinge, a strap hinge, or other types of hinges as understood by a person having ordinary skill in the art.

Figure 2:
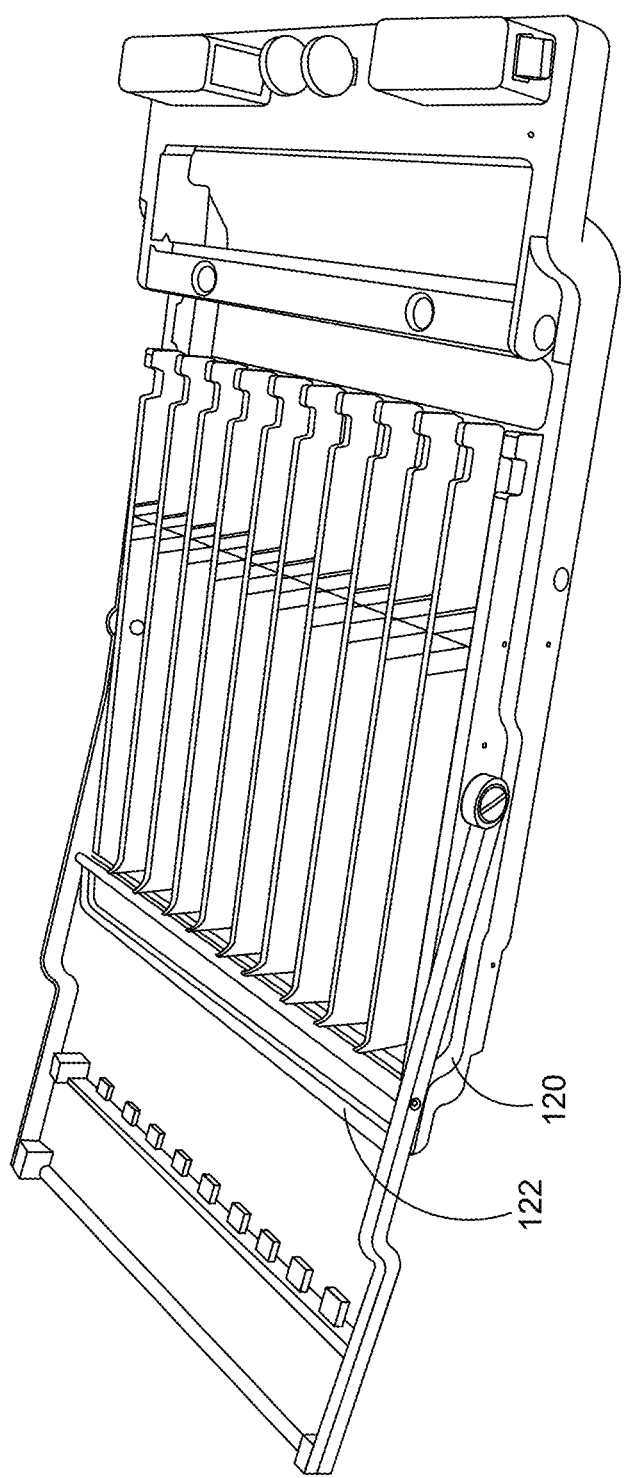
FIG. 2 illustrates an example of a cartridge tray in an opened position to be used in a biochemical test.

The hinged frame 120 is capable to rotate to an opened position or a closed position. For instance, FIGS. 1 and 2 illustrate a hinged frame 120 being rotated to the closed position and the opened position, respectively. The hinged frame includes a horizontal push bar 122 configured to apply a downward force to test cartridges 180 received in the plurality of slots 112 when the hinged frame 120 is in the closed position. A combination of the slots 112 and the horizontal push bar 122 secures the test cartridges in the tray when the hinged frame 120 is in the closed position. In some embodiments, the slots 112 and the horizontal bar 122 secure test cartridges 180 such that a robotic arm of the immunoassay test apparatus is capable to open caps of the test cartridges 112 secured on the tray without any movement of the test cartridges 112 relative to the tray 100 and pick up a probe from a test cartridge 180 to perform a biochemical test.

The push bar 122 helps preventing lateral movement of the cartridges in the tray. In some embodiments, after the loaded tray is inserted into a test apparatus, the test apparatus shakes the tray before conducting test. The push helps to fix the cartridges in the tray, to prevent lateral movement and accelerating movement of the cartridges relative to the tray.

The locking mechanism 130 is to lock the hinged frame 120 in the closed position when the hinged frame 120 rotates to the closed position. In an embodiment illustrated in FIG. 1, the lock mechanism 130 includes a spring-loaded pin 132 to reversibly lock the hinged frame 130 in the closed position when the hinged frame 130 rotates to the closed position. The lock mechanism 130 can further include two such spring-loaded pins 132 to lock both left and right side of the hinged frame 130. As illustrated in FIG. 1, the outward ends of the spring-loaded pins 132 can have tilted slope surface so that the hinged frame 120 can be rotated into the closed position passing the tilted slope surface. When the hinged frame 120 contacts the tilted slope surface, the spring-loaded pins 132 retract. After the hinged frame 120 reaching the closed position, the spring-loaded pins 132 return to the extruded positions to lock the hinged frame 120 in the closed position.

The cartridge tray 100 can further include a release mechanism 140 to unlock the hinged frame 120 from the closed position. For instance, as shown in FIG. 1, the release mechanism 140 can include two tabs for releasing the test cartridges 180 from the slots 112 by a finger motion. The release mechanism 140 can unlock the hinged frame from the closed position by applying a force to the tabs 140 to retract the spring-loaded pin 132 so that the test cartridges 180 can be disposed of from the plurality of slots 112. When a user uses fingers to squeeze the tabs 140, the spring-loaded pins 132 retract, the hinged frame 130 can be freely rotates to the opened position.

The cartridge tray 100 can be manufactured such that the center of mass of the tray locates at a geometric center of the tray 100. This is helpful when the test apparatus need to secure the tray 100 and shake the cartridge 180 in the tray 100.

FIG. 2 illustrates that the hinged frame 120 rotates to an opened position. Without the push bar 122 of the hinged frame 120 pushing the cartridges 180 against the slots 112, the cartridges 180 can be freely removed from the slots 112 and be replaced or disposed of.

Test Cartridge

Figure 3:
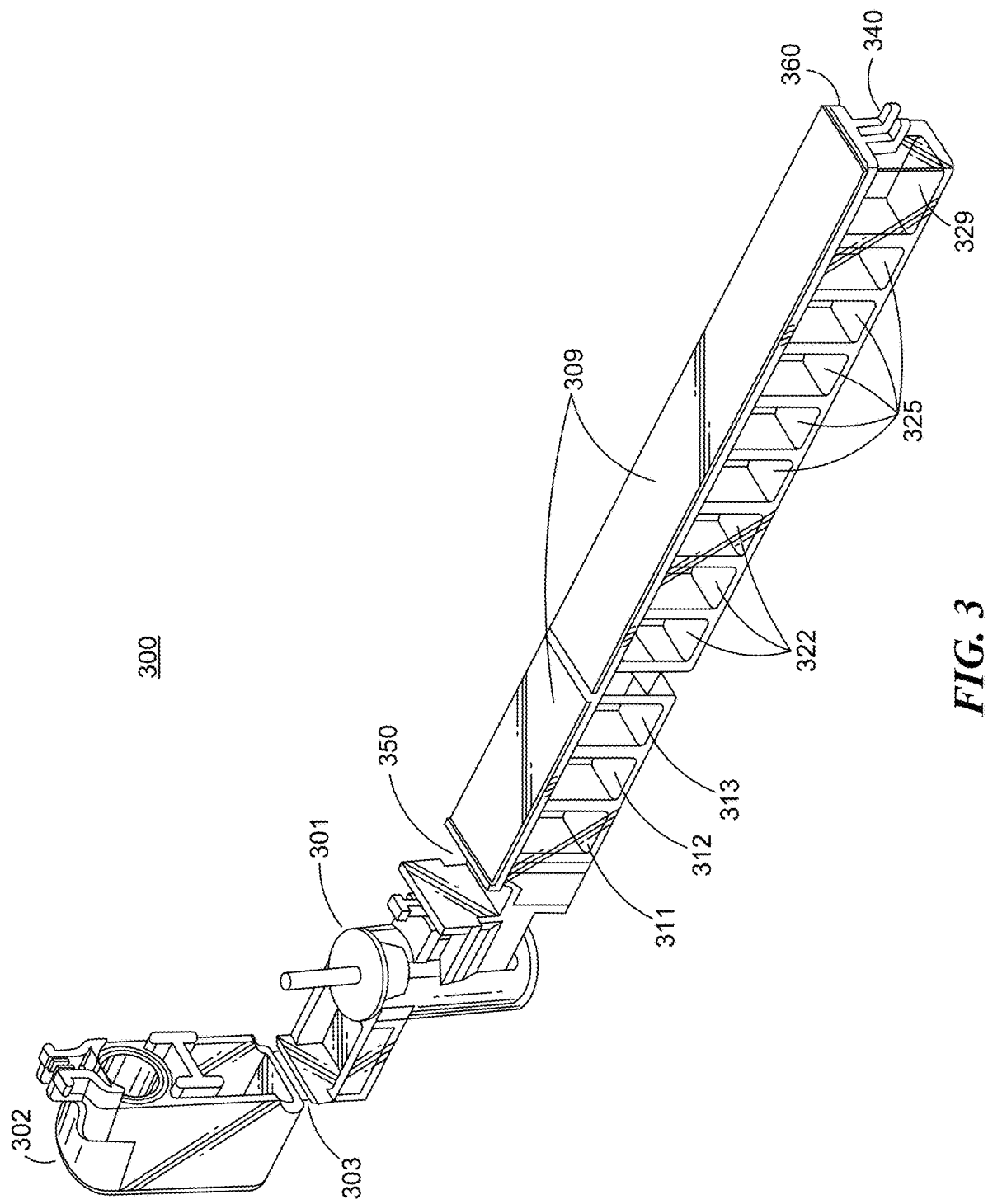
FIG. 3 illustrates an example of a test cartridge that can be inserted into a cartridge tray.

FIG. 3 illustrates an example of a test cartridge of the present invention. One or more test cartridges can be placed in a cartridge tray (e.g. tray 100 in FIG. 1) as an assembly ready for automated biochemical tests. In one embodiment (FIG. 3), cartridge 300 comprises a probe well 301 and a protective cap 302 to accommodate and secure the probe. The probe well 301 serves as a protective container for the probe. In one embodiment, the cap 302 is mechanically coupled to the probe well 301 via a hinge 303. After the probe is inserted in the probe well 301, the cap 302 is folded over the probe well 301 to fully enclose the probe. The probe may be vertically stored inside the probe well 301 when the protective cap 302 is in a closed position.

The cartridge 300 can include lips 340 to be inserted into cavities (not shown) on the side walls of the cartridge tray 100 to further secure the cartridge 300 in the slots 112 of the tray 100.

The cartridge 300 further includes a recess portion 350 for receiving a horizontal push bar (e.g. push bar 122 in FIG. 1). The recess portion may have a bottom surface and two side surfaces to confine a section of the push bar in the space within the recess portion 350. In other words, the horizontal push bar is bound by a bottom surface and two side surfaces of the recess portion 350 of the test cartridge when the hinged frame 120 is in the closed position.

The test cartridge 300 may further comprises a flange 360 that is wider than the wells below. The flange 360 is designed for the cartridge 300 to sit on top of one of the slots 112 when the test cartridge 300 is received in the slot 112. As illustrated in FIG. 1, the flange sits against the slot 112 prevent the cartridge 180 from moving downward against the tray 100, white the push bar 122 prevent the cartridge 180 from moving upward way from the tray 100. The flange and the horizontal push bar confine the test cartridge 300 such that the test cartridge 300 cannot move vertically relatively to the tray 100 when the hinged frame 120 is in the closed position.

The cartridge 300 may comprise two separate compartments of wells. The first compartment comprises a sample well 311, and one more reagent wells. In an embodiment as illustrated in FIG. 3, the first compartment comprises a first reagent well 312 and a second reagent 313. For example, the biotin reagent in the first reagent well 312 comprises a biotinylated second antibody. The second reagent well 313 contains a labeled streptavidin. The label may be any typical label used in diagnostic kits, such as fluorescent, chemiluminescent, or enzyme labels. For instance, the biotin and streptavidin reagents may be in dry format or in a wet format of about 5 μL liquid. In some other embodiments, the wells 312 and 313 can be used for storing reagents other than the biotin reagent and streptavidin reagent.

The second compartment comprises reconstitution wells 322, wash wells 325, and a measurement well 329. These wells may contain fluids such as buffer and diluent. The reconstitution wells 322 contain buffer or diluents to be dispensed into the sample, biotin and streptavidin wells 311-313 for reconstituting the dry reagents in the these wells. The liquids in reconstitution wells may be transferred to wells 311-313 using pipettes. Each of the wash wells 325 contains a first aqueous solution to wash the probe after binding steps in the sample, biotin, and streptavidin wells 311-313. In some other embodiments, there can be a different arrangement for the reconstitution and wash wells. For instance, in an alternative embodiment, there can be two reconstruction wells and six wash wells. Other numbers of reconstruction wells and wash wells are possible, as readily understood by a person having ordinary skill in the art. For instance, the cartridge can have preferably 2~6 reconstruction wells, more preferably 2~4 reconstruction wells. The cartridge can also have preferably 2~12 wash wells, more preferably 3~6 wash wells.

The measurement well 329 contains a second aqueous solution. In one embodiment, the second aqueous solution is the same as the first aqueous solution. The measurement well 329 has a light transmissive bottom, which may be transparent or translucent. The light transmissive bottom is used for an optical reading during the immunoassay test. The optical signal at the bottom tip of the probe is read through the light transmissive bottom. In one embodiment, a laser beam is projected through the light transmissive bottom to the bottom tip of the probe excite a die of a fluorescent tag; the fluorescent signal is collected through the light transmissive bottom. In some embodiment, the thickness of the light transmissive bottom is less than 1 mm. The first and second compartments are separate by a distance to prevent liquid penetration from wells containing liquids to wells containing dry reagents.

The technique of fluorescent signal detection in a measurement well is discussed in details in Patent Application No. 2011/0312105, the content of which is incorporated herein by reference in its entirety.

The top opening of the wells is sealed with any suitable materials, e.g., foil or film 309. The seal is penetrable. The wells may be opened by piercing the seal by a manual or automated device. To achieve better sealing, rims, i.e. small raised lines, are built around the opening of the wells and the edges round the wet and/or dry well areas.

In one embodiment, the cartridge is used to conduct an immunoassay test. Using a pipettor dispensing subsystem, about 50 μL of diluent is transferred from reconstitution wells to each of the sample, biotin, and streptavidin wells on the cartridge. An aliquot of about 20 μL of sample is transferred from a sample tube to the sample well by a pipettor. The cap of the probe well is opened and the probe is transferred to the sample well and the bottom tip of the probe is immersed in the liquid sample mixture. The probe incubates with the liquid sample mixture for a period of time. Afterward, the probe is sequentially transferred to one or more (e.g. 2-4) wash wells. Subsequently, the probe is transferred to a biotin reagent well and incubated for a period of time. The probe is sequentially transferred to wash wells. Afterward, the probe is transferred to a streptavidin reagent well and incubated for a period of time. The probe is sequentially transferred to wash wells and lastly transferred to a measurement well. The labeled streptavidin at the bottom tip of the probe is detected through a light transmissive window of the measurement well.

A sample well is a well that receives a sample containing an analyte. A sample well can be a blank well, or it can contain detergents, blocking agents and various additives for the immunoassay, either in a dry format or in a wet (liquid) format. In human blood samples, heterophile antibodies (antibodies that bind IgG from other species) and rheumatoid factor are common interfering substances for immunoassays. There are a variety of blocking agents minimizing this form of interference. For examples, blocking agents include IgGs from different species such as murine IgGs, heat aggregated IgG, crosslinked IgG, and commercially available heterophile blockers. The wet format of blocking agents typically contains a small liquid volume (<10 μL, e.g., 5 μL). The dry format of blocking agents includes a lyophilization cake, powder, tablet or other formats typical in diagnostic kits; the dry format is to be reconstituted to a wet format by a reconstitution buffer and/or sample. The sample well serves as a primary reaction chamber for the reaction between the analyte in the sample and the analyte-binding molecules coated on the probe to form an immunocomplex.

The cartridge comprises one or multiple reagent wells. The reagent wells contain reagents that react with the immunocomplex and generate a signal for detection. The reagents can be in a wet format or in a dry format. The wet format contains a reagent in an assay buffer. The wet format is typically in a small liquid volume (<10 μL, e.g., 5 μL). An assay buffer typically includes a buffer (e.g., phosphate, tris), a carrier protein (e.g., bovine serum albumin, porcine serum albumin, and human serum albumin, 0.1-50 mg/mL), a salt (e.g., saline), and a detergent (e.g., Tween, Triton). An example of an assay buffer is phosphate buffered saline, pH 7.4, 5 mg/ml bovine serum albumin, 0.05% Tween 20. The assay buffer optionally contains a blocking agent in an amount of 1-500 μg/mL. The final formulation will vary depending on the requirements of each analyte assay. The dry format is the dry form of the reagent in an assay buffer. The dry format includes lyophilization cake, powder, tablet or other formats typical in diagnostic kits. The dry format is to be reconstituted to a wet format by a reconstitution buffer.

In one embodiment, the cartridge contains two or more reagent wells. For example, a first reagent well contains second antibody molecules conjugated with a first member of a binding pair, and a second reagent well contains a second member of the binding pair labeled with reporters. For example, the first reagent well is a biotin reagent well containing a biotinylated second antibody directed against the analyte. The second reagent well is a streptavidin reagent well containing streptavidin labeled with reporters to amplify signal. The reporters can be any of those typically used in diagnostic kits, i.e. fluorescent, chemiluminescent, or enzyme labels.

The cartridge comprises one or more washing wells each containing an aqueous solution. The wash wells contain a wash buffer to wash the probe after binding steps in the sample well and reagent well(s). One to four wash wells (e.g., 1, 2, 3, or 4 wells) are dedicated for washing after each binding step. Wash buffers contain detergents. Any detergent typically used in immunoassays (e.g., Tween, Triton) can be used in this invention.

The cartridge comprises a measurement well having an optically clear bottom that enables the detection of the labeled-immunocomplex bound to the bottom tip of the probe. The measurement is through the bottom of the well. The measurement well contains a liquid solution. In the case when the label is an enzyme, the aqueous solution contains a substrate of the enzyme.

In one embodiment, some of the wash wells are served for the purpose of reconstituting the dry forms in the sample well and reagent well(s). In this case, no additional reconstruction wells are needed.

In another embodiment, the cartridge further comprises reconstitution wells that contain reconstitution buffer to be dispensed into the sample wells and reagent wells to reconstitute the dry forms in the sample well and reagent well(s). The reconstitution buffer can be a buffer such as phosphate-buffer saline. The reconstitution buffer can additionally include other additives (carrier protein, blockers, detergents, etc.) contained in the assay buffer. Several configuration of the reconstitution wells are feasible; for example, there can be several wells (50~200 μL, e.g. 100 μL) each dedicated to each one of the sample and reagents, or there can be a single well with a sufficient volume for all the sample and reagents.

Figure 4:
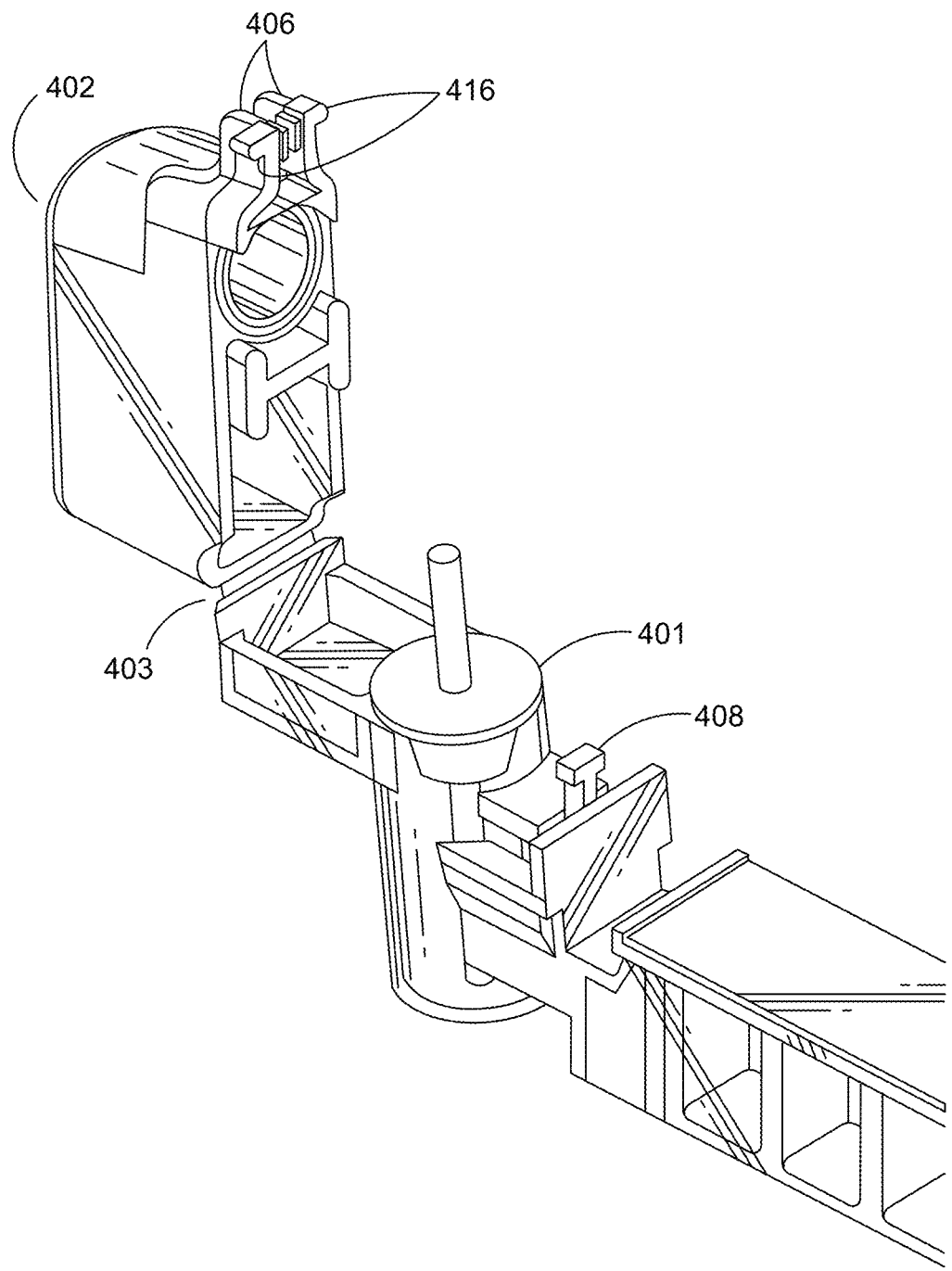
FIG. 4 illustrates an example of a probe well and a cap of a test cartridge.

FIG. 4 illustrates an example of the probe well 401 and the cap 402 of the cartridge, according to one embodiment of the present invention. The cap 402 is hinged to the probe well 402 via a hinge 403 sot that the cap 402 can rotate to a closed position or an open position. The open position of the cap 402 is shown in the FIG. 4. The probe well 401 can have a recess (not shown) inside of the opening of the probe well 401. A cushion may be placed on the recess 404 to support the probe when the probe is stored vertically. The cap 402 may have a pair of clamping arms 406; there are a corresponding pole 408 near the probe well 401. When the cap 402 is in a closed position, the clamping arms 406 are pushed over the extrusion on the pole 408 so that the cap 401 is locked in the closed position. An ordinary skilled person in the art will readily use other shapes or mechanisms to serve the purpose of the clamping arms.

Figure 5:
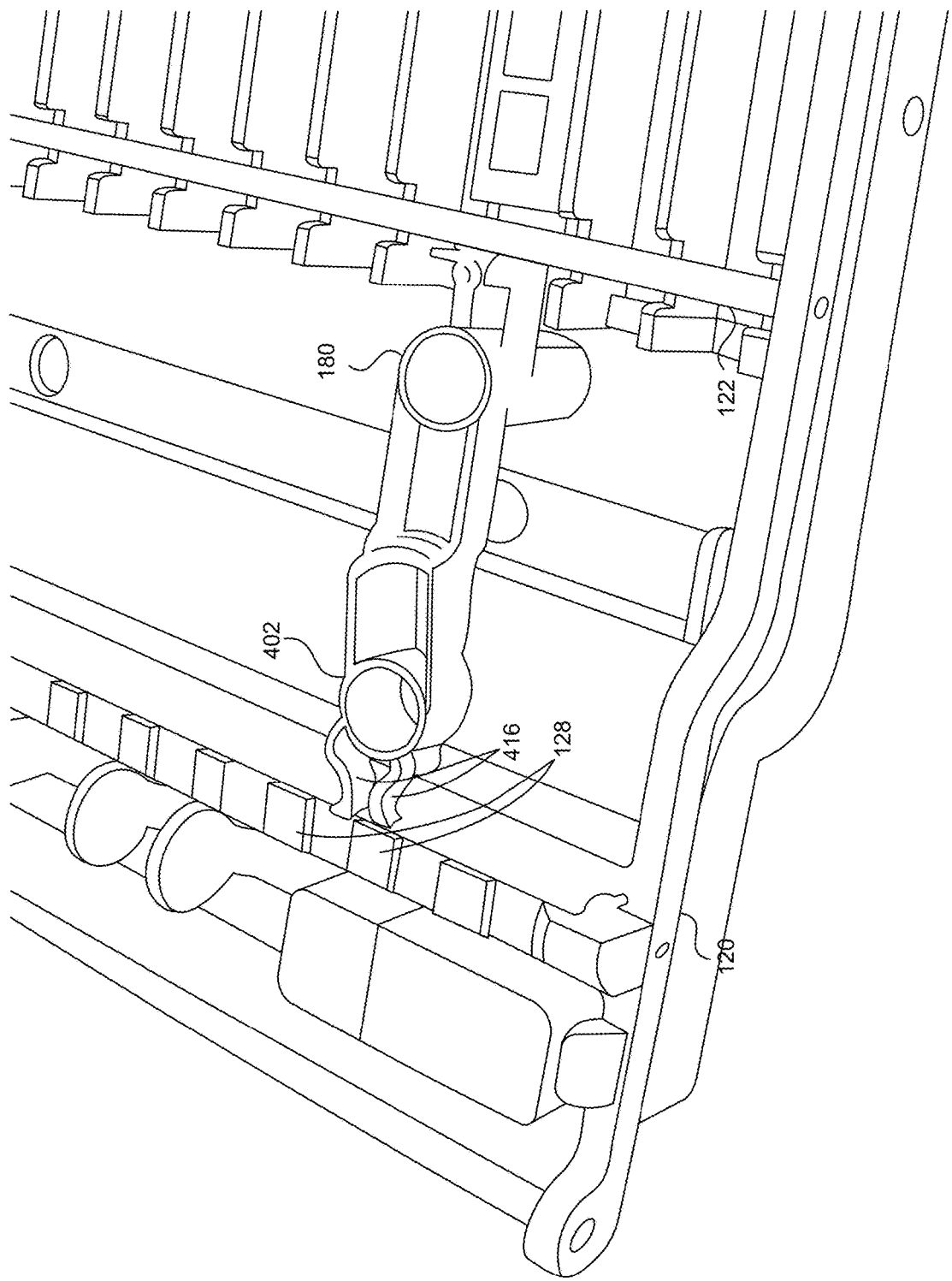
FIG. 5 illustrates an example of a portion of a cartridge tray and a test cartridge.

The clamping arms 406 can further include outward extrusions 416. As illustrated in FIG. 5, the cap 402 of the cartridge 180 can be also secured on a tray when the cap 402 is opened. After the push bar is applied to push the cartridge 180 against the slots 112, the cap 402 can be opened to pass one or more tabs 128 attached to the hinged frame 120 of the tray to secure the cap 402 from reverting back, so that the cap 402 does not accidentally close itself during the biochemical test such as an immunoassay test. A user can pinch the two clamping arms 406 toward each other when the user pushes the cap 402 toward the tabs 128. Since the two clamping arms 406 are pinched together, the outward extrusions 416 can pass the tabs 128 without being blocked. Once the outward extrusions 416 of the clamping arms 406 pass the tabs 128, the user releases the fingers from the clamping arms 406. The clamping arms 406 return to their original positions. The space between the tabs 128 are designed such that the extrusions 416 in the unforced positions cannot pass through the tabs 128. Therefore, the cap 402 is locked in a position by the tabs 128. Such a mechanism guarantees that the cap 402 does no accidentally revert back to interfere with the probe conducting the biochemical test in the wells.

Figure 6:
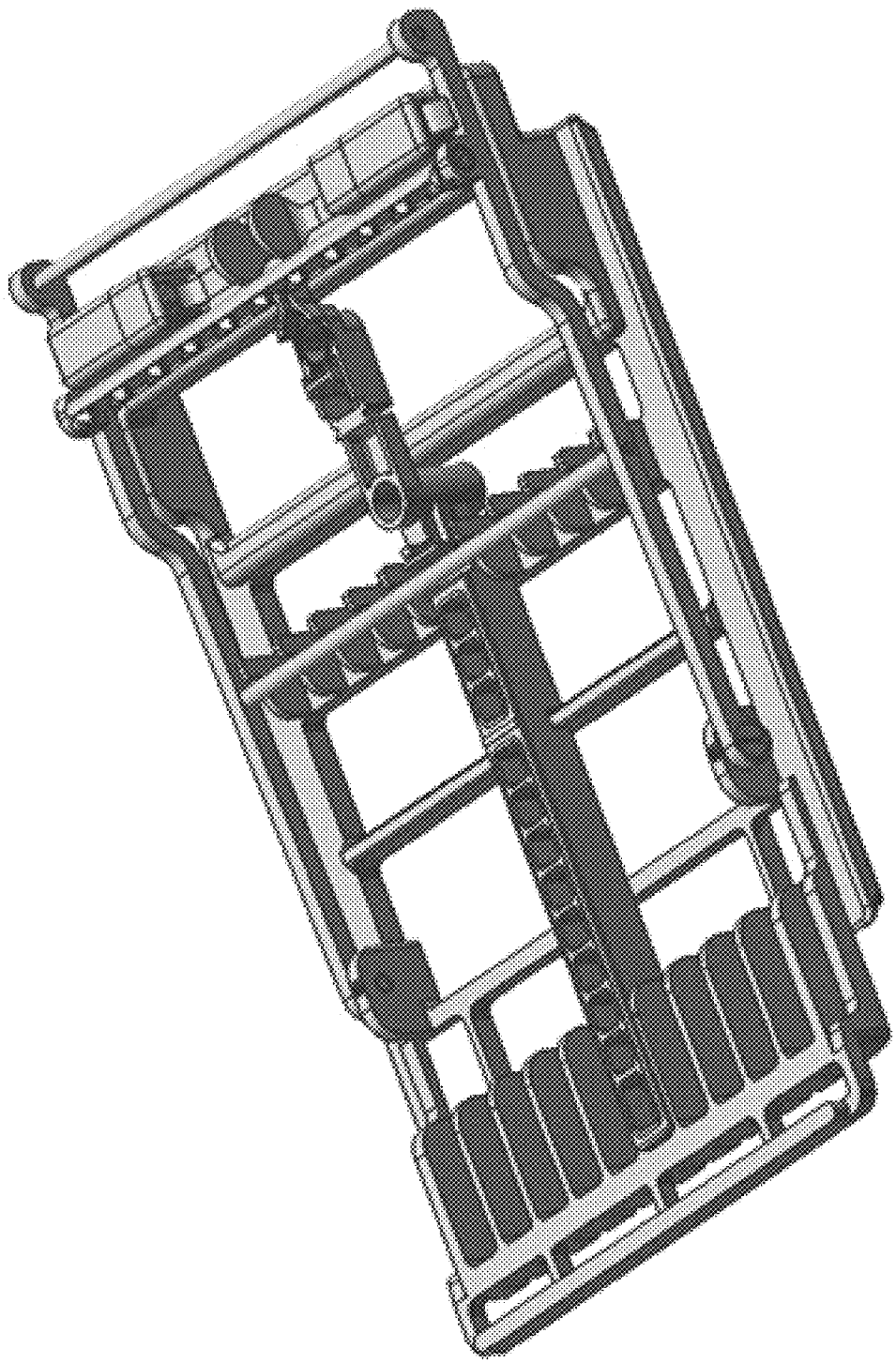
FIG. 6 illustrates an example of a test cartridge secured in a cartridge tray.
Figure 7:
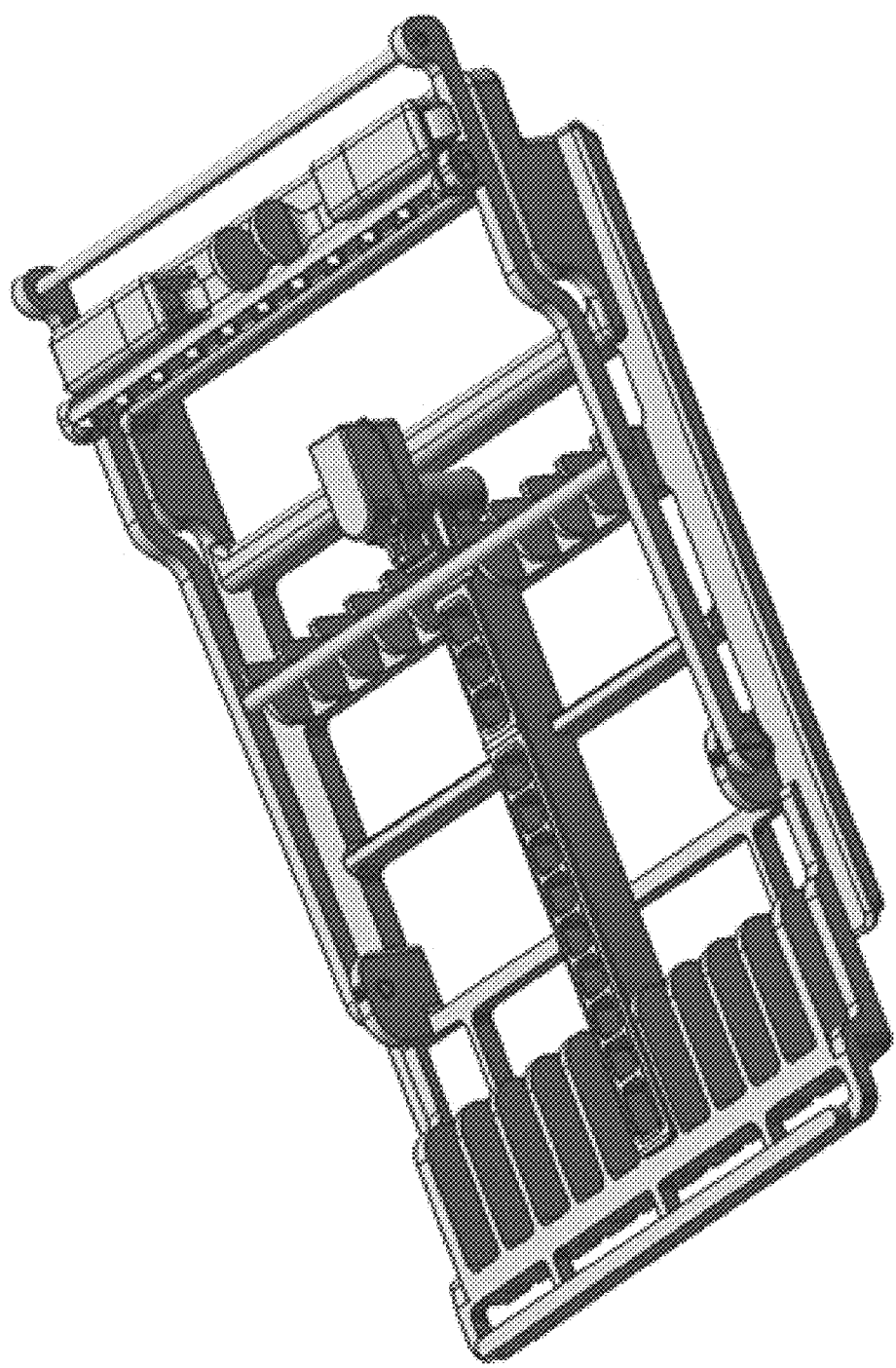
FIG. 7 illustrates an example of a test cartridge in a cartridge tray with cap closed.
Figure 8:
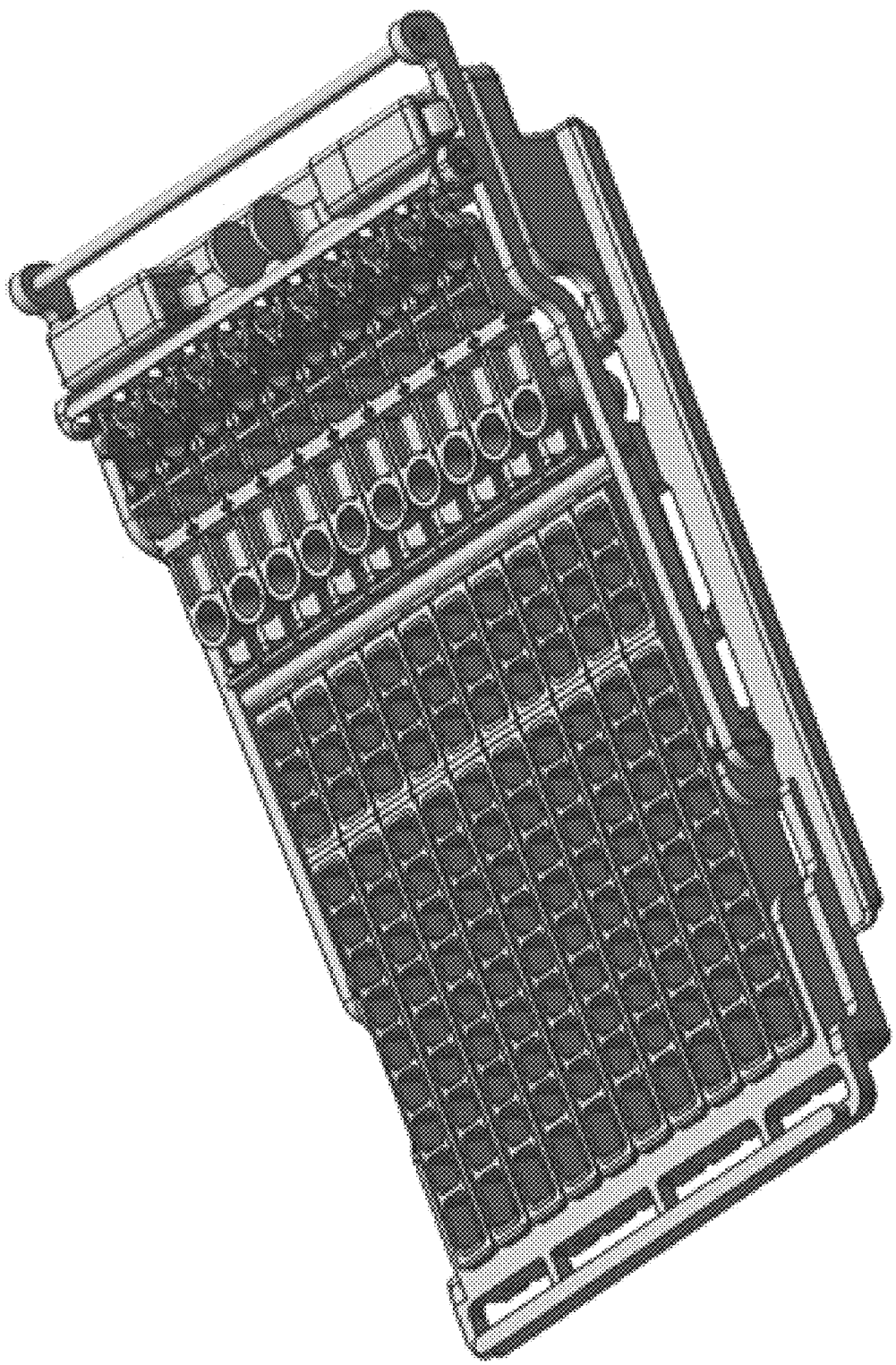
FIG. 8 illustrates an example of a cartridge tray holding multiple test cartridges.

FIG. 6 illustrates a test cartridge secured in a cartridge tray. Similar to FIG. 5, the space between the tabs are designed such that the extrusions in the unforced positions cannot pass through the tabs. The cap is locked in a position by the tabs. After conducting a biochemical test, the test apparatus can release the cap from the locked position by squeezing the outward extrusions 416 of the test cartridge and close the cap. FIG. 7 illustrates a test cartridge in a cartridge tray with the cap closed. FIG. 8 illustrates a cartridge tray holding multiple test cartridges.

Cartridge Tray with Holder

Figure 9:
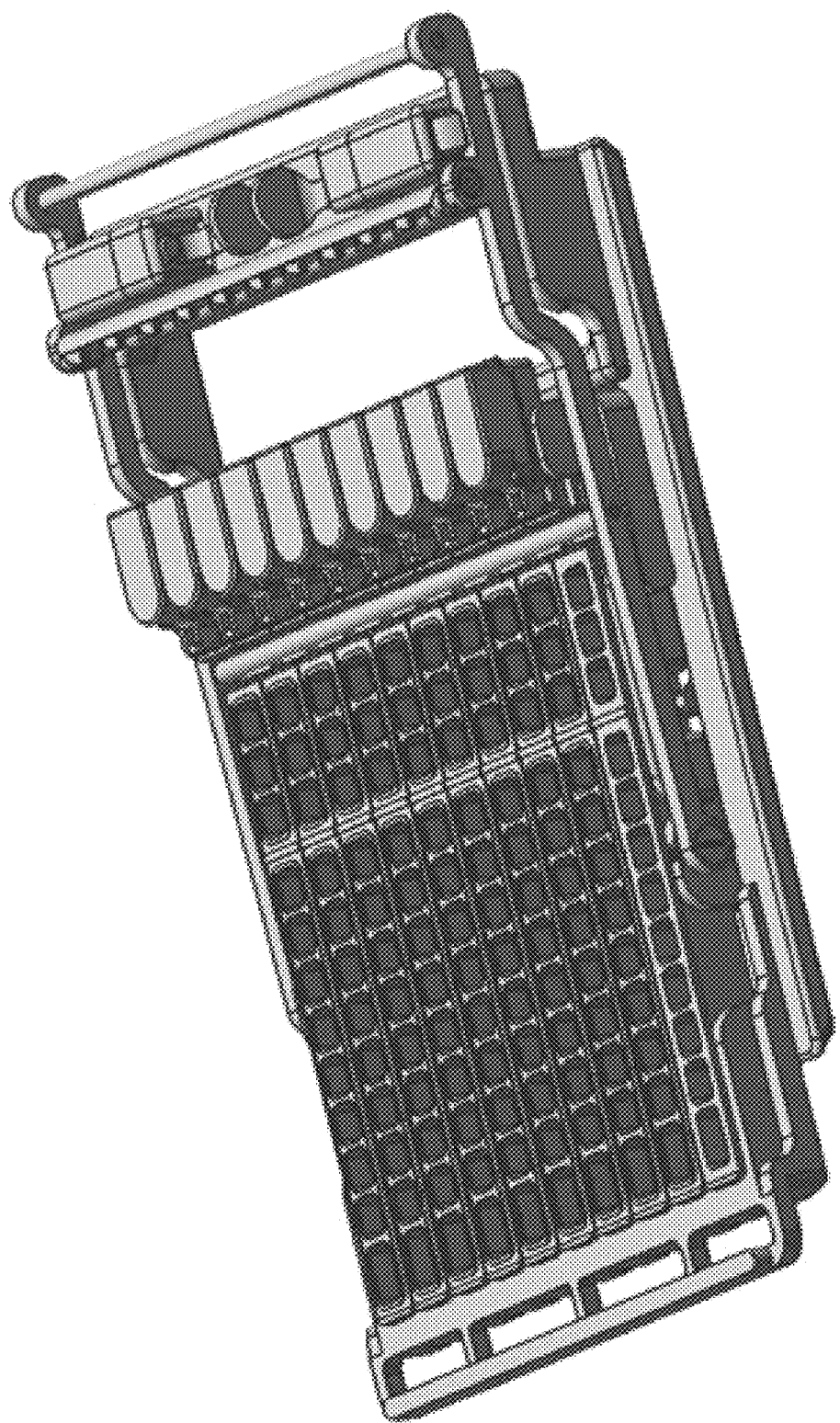
FIG. 9 illustrates an example of a cartridge tray that accommodates a cartridge holder carrying one or more test cartridges.
Figure 10:
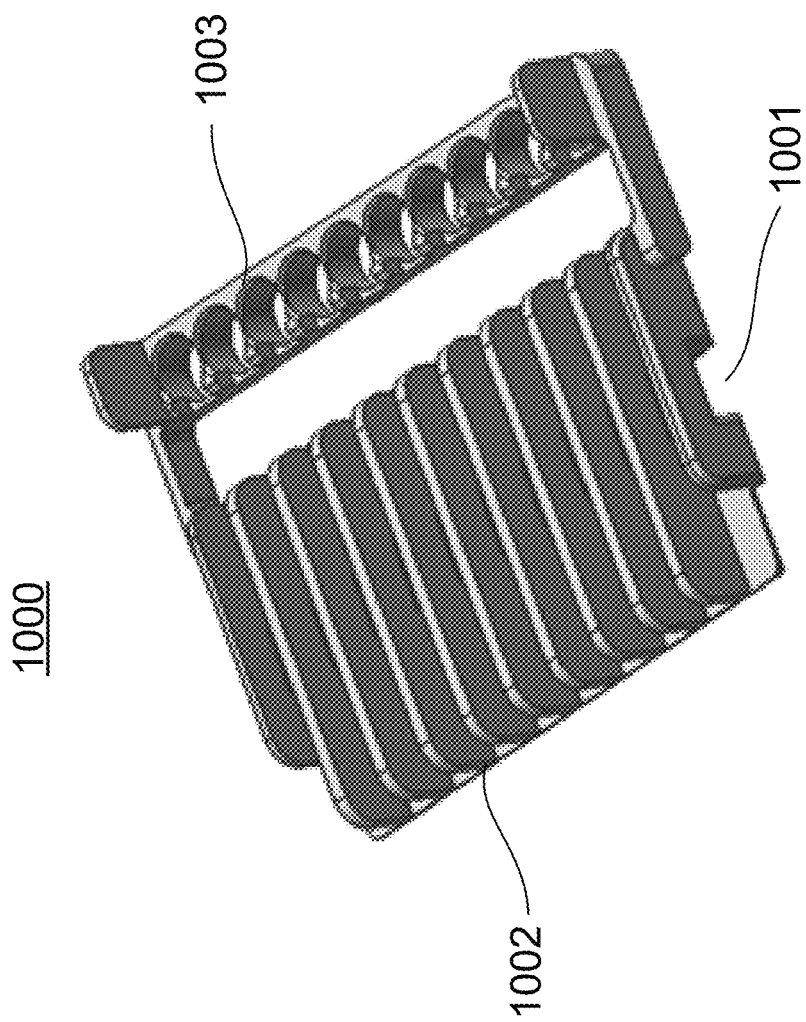
FIG. 10 illustrates an example of a cartridge holder can be loaded into a cartridge tray.

FIGS. 9-21 illustrate another example of cartridge tray of the present invention. FIG. 9 illustrates a cartridge tray that accommodates a cartridge holder carrying one or more test cartridges. The cartridge holder can carry preferably 2~16 test cartridges, more preferably 4~10 cartridges. FIG. 10 illustrates a cartridge holder can be loaded into a cartridge tray. The cartridge holder 1000 includes a notch 1001 on the bottom. When the cartridge holder 1001 is placed into a cartridge tray, the notch 1001 sites on top of a bar of the cartridge tray such that cartridge holder 1000 cannot move laterally relative to the cartridge tray. The cartridge holder 1000 further includes a plurality of slots 1002 to receive one or more test cartridges. The slots 1002 can have shapes consistent with the outer shapes of the test cartridge. For instance, each of the plurality of slots 1002 can have a substantially rectangular shape for receiving a test cartridge, while the test cartridge has a substantially rectangular outer shape. The cartridge holder 1000 also includes a plurality of holes 1003. The inner shapes and dimensions of the holes 401 are designed to accommodate the bottom of the probe well 401 of the test cartridge (illustrated in FIG. 4).

Figure 11:
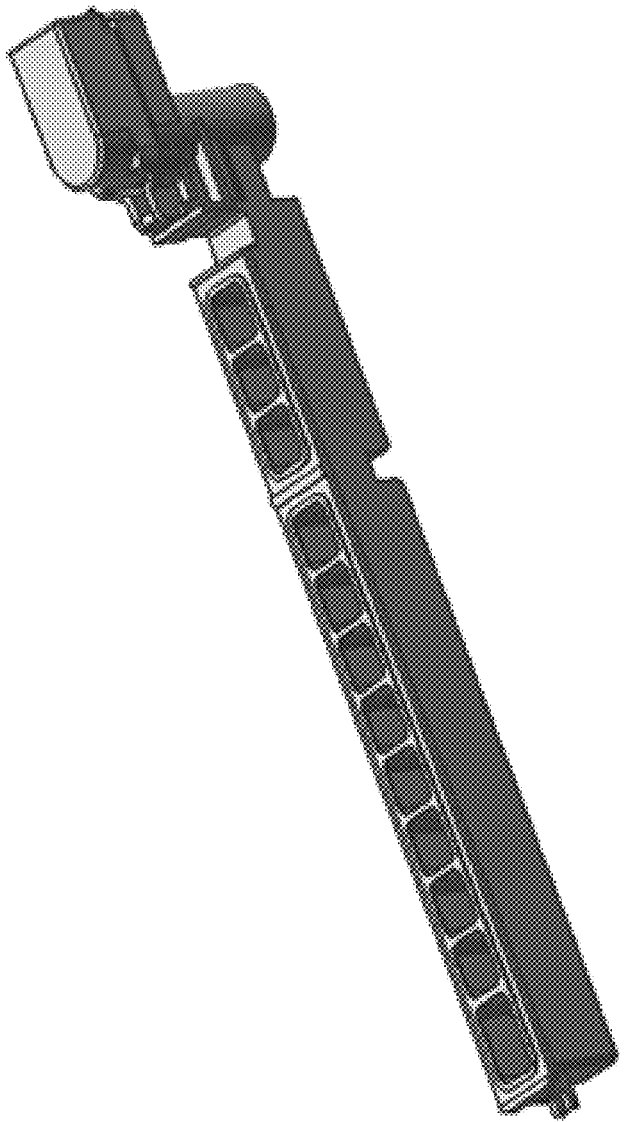
FIG. 11 illustrates an example of a test cartridge can be loaded into a cartridge holder.
Figure 12:
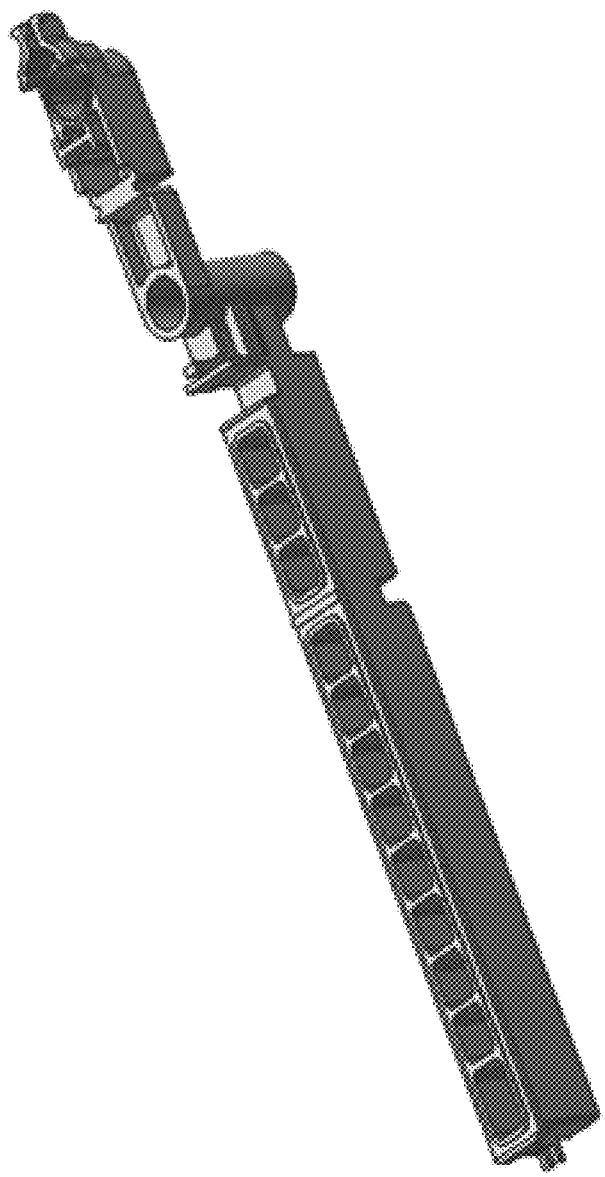
FIG. 12 illustrates an example of a test cartridge with its cap opened.
Figure 13:
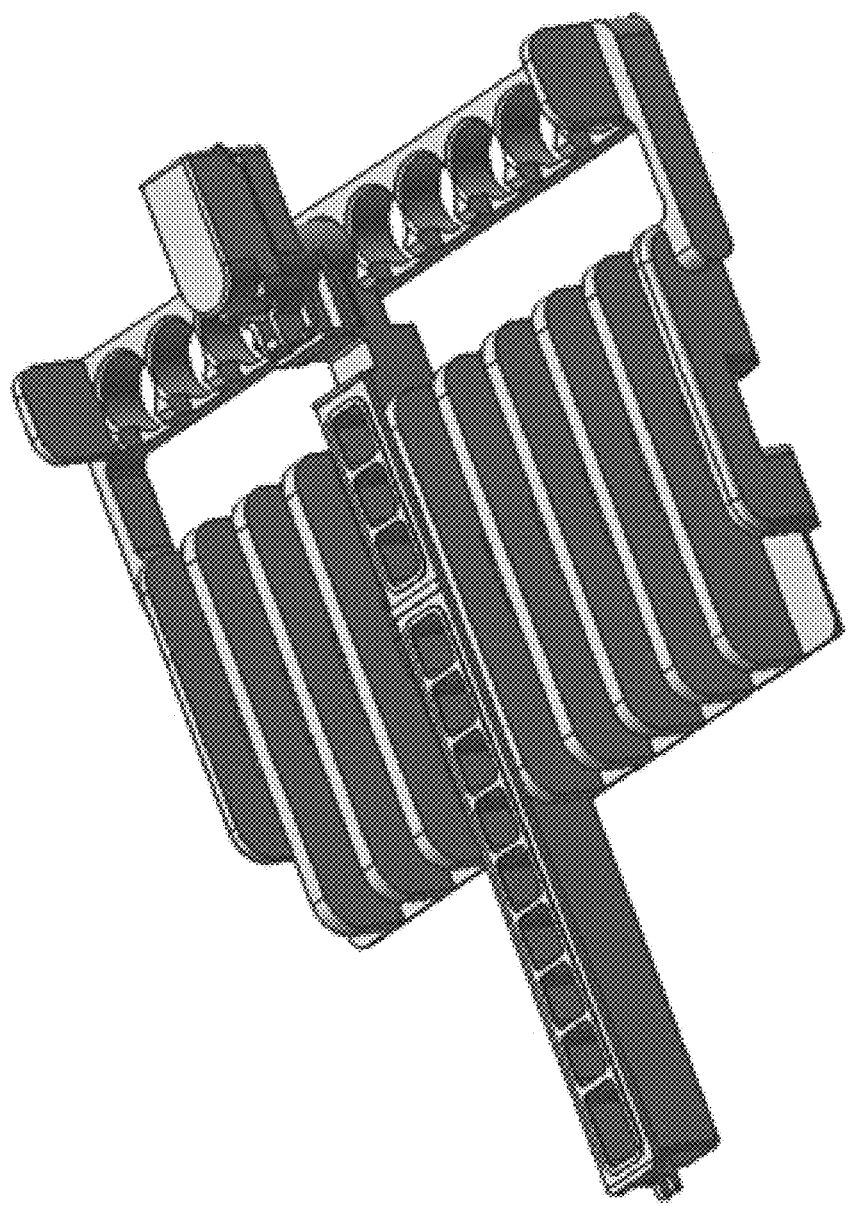
FIG. 13 illustrates an example of a test cartridge loaded into the cartridge holder.
Figure 14:
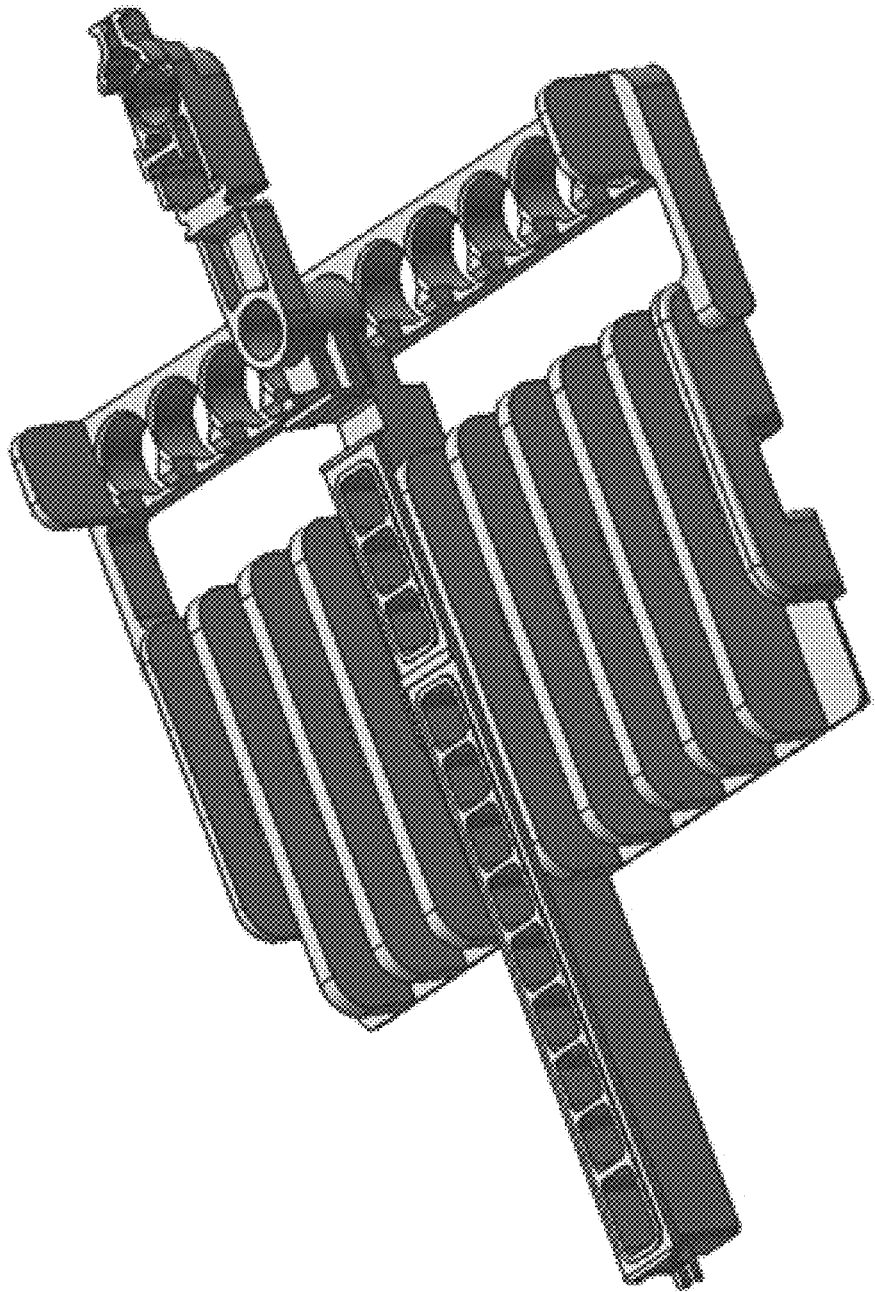
FIG. 14 illustrates an example of a test cartridge in a cartridge holder with its cap opened.
Figure 15A:
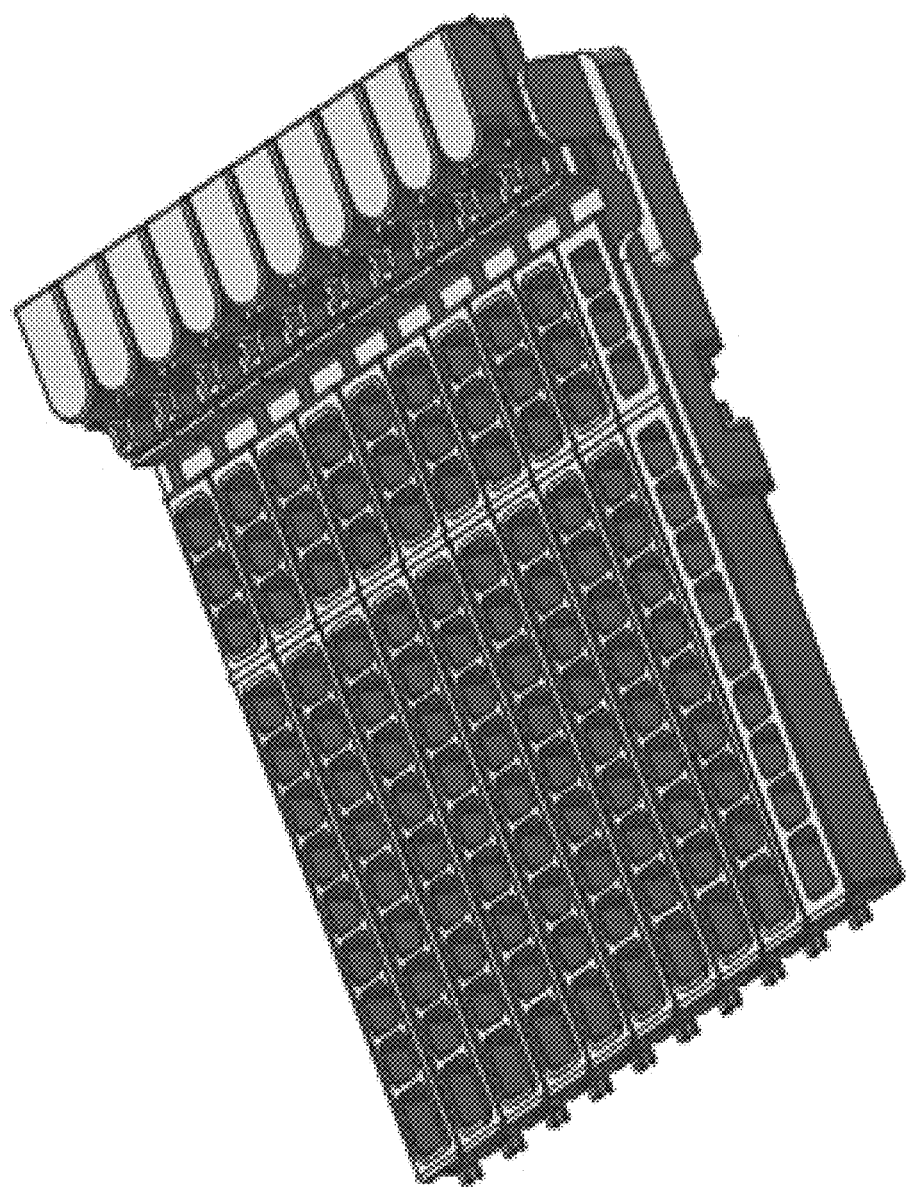
FIG. 15A illustrates a cartridge holder that holds multiple test cartridges with caps closed.
Figure 15B:
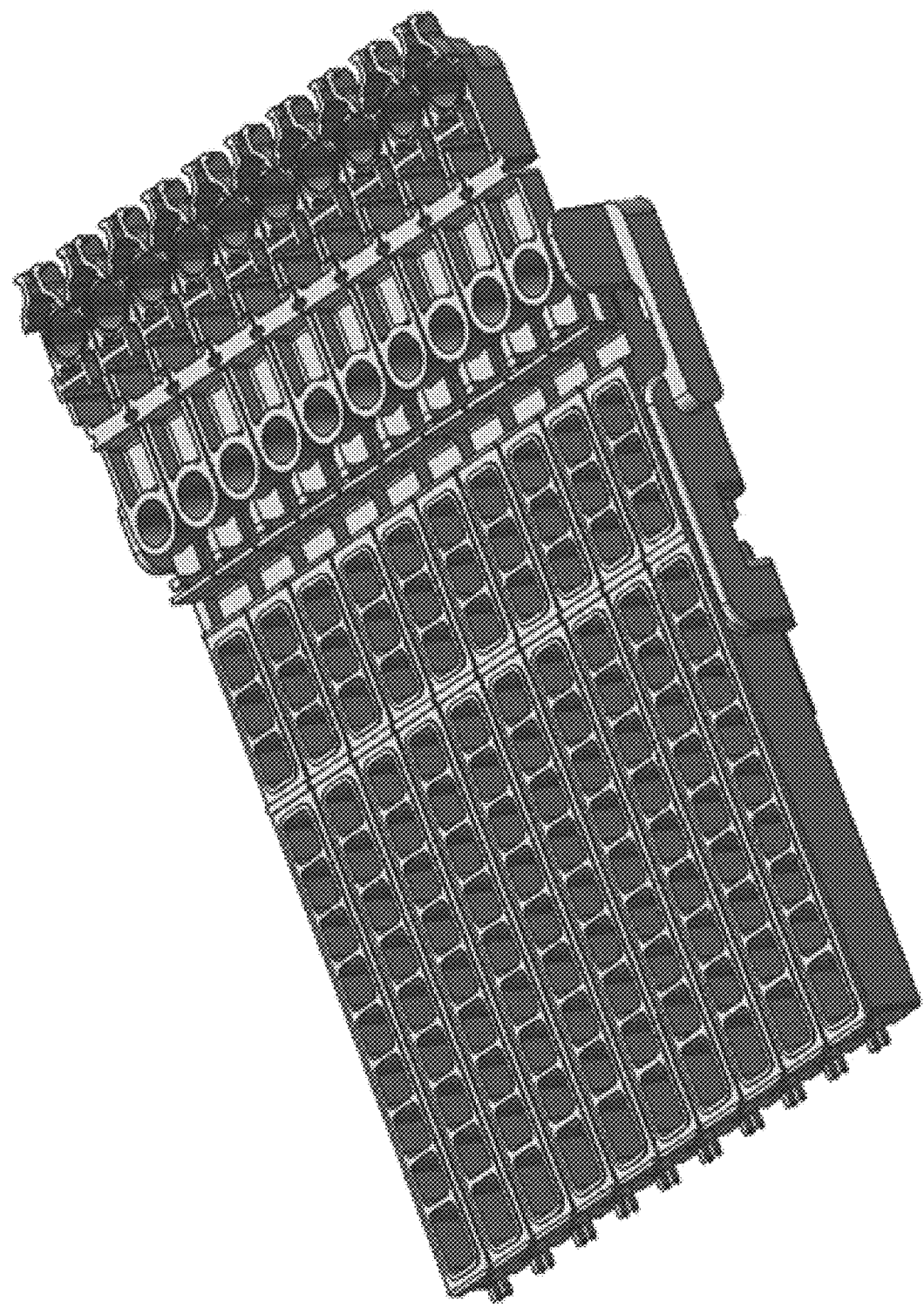
FIG. 15B illustrates a cartridge holder that holds multiple test cartridges with caps opened.
Figure 16:
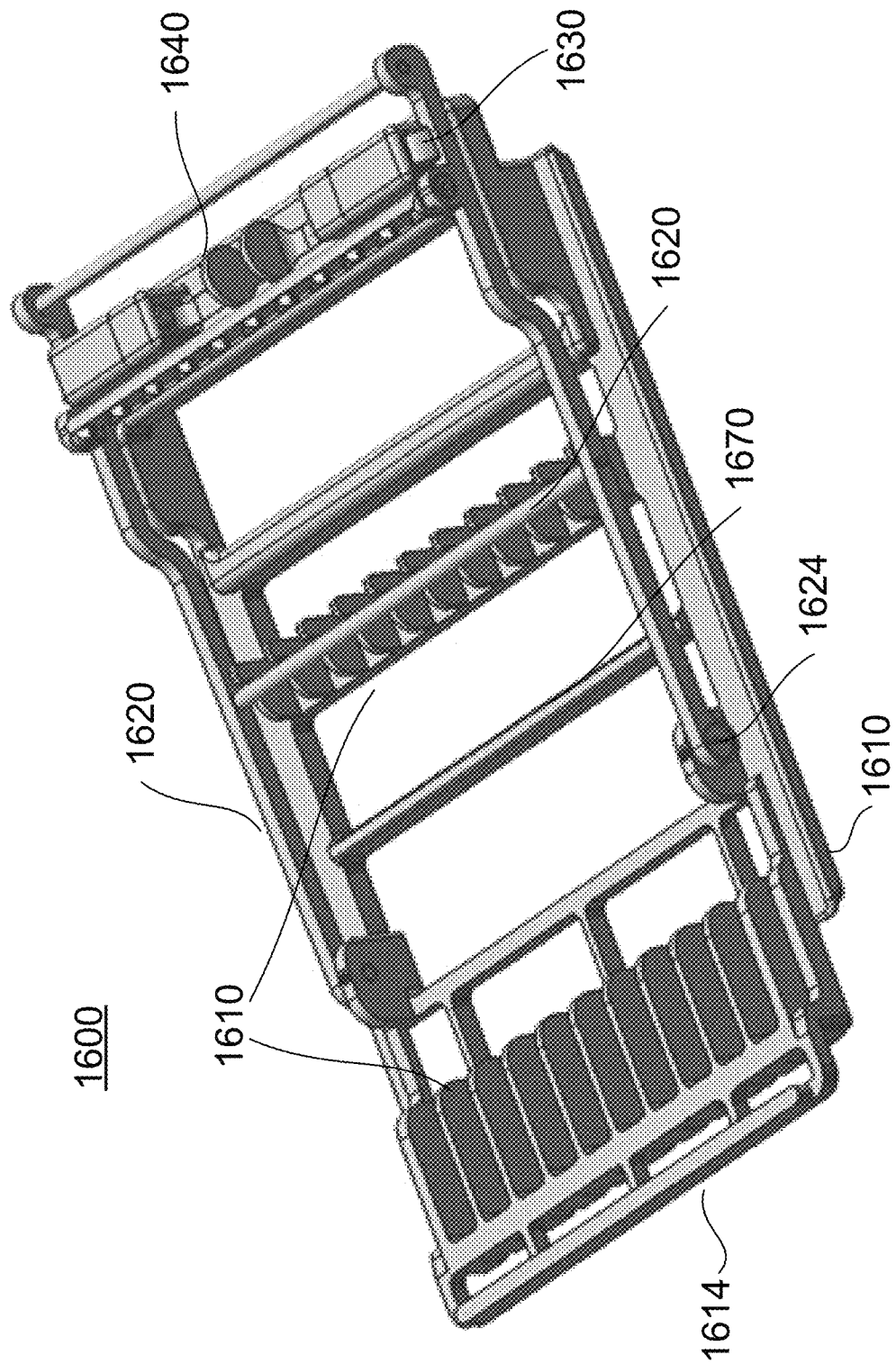
FIG. 16 illustrates an example of a cartridge tray that can accommodate a cartridge holder.

FIG. 11 illustrates an example of a test cartridge can be loaded into a cartridge holder. The cap of the test cartridge is closed. FIG. 12 illustrates a test cartridge with its cap opened. FIG. 13 illustrates a test cartridge loaded into the cartridge holder. Due to the shapes of the slots and holes of the cartridge holder, the test cartridge cannot move laterally relative to the cartridge holder. FIG. 14 illustrates a test cartridge in a cartridge holder with its cap opened. The cartridge holder can accommodate multiple test cartridges depending on the number of the slots. FIG. 15A illustrates a cartridge holder that holds totally 10 test cartridges. Each slot of the cartridge holder holds one of the test cartridges. FIG. 15B illustrates a cartridge holder that holds multiple test cartridges with their caps opened.

During operation of a test apparatus, the test apparatus moves the cartridge tray into the apparatus to position the cartridge tray as necessary for the apparatus to drop test probe at precise locations in the wells of the test cartridges secured in a holder in the cartridge tray. In the embodiment shown in FIG. 16, the cartridge tray 1600 includes a base member 1610, a hinged frame 1620 and a locking mechanism 1630.

The base member 1610 includes a plurality of slots 1612 within the base member 1610. The base member 1610 can have outside surfaces that include grooves adapted to guide the tray into a tray drive of a test apparatus. For instance, the grooves can be arranged in parallel with an axis of the tray 1600. The grooves guide the tray 1600 into a test apparatus when a user inserts the tray 1600 into the test apparatus. The cartridge tray 1600 can further include a handle 1614 attached to the base member 1610 such that a test apparatus can grip the handle 1614 and move the tray 1600 into a tray drive of the test apparatus. Alternatively, the base member 1610 and/or the hinged frame 1620 can include mechanical features (e.g., grooves, notches, bars, tabs, etc.) so that the test apparatus can push or pull the mechanism features to move the tray cartridge.

The base member 1610 and/or the hinged frame 1620 can include various mechanical features to help the test apparatus to move the cartridge tray or to secure the position of the cartridge tray. For example, the base member 1610 can include multiple vertical notches on the sides of the base member 1610, such that the test apparatus can use pins aligned into the grooves to secure the position of the cartridge tray. The directions of the vertical notches are parallel to the direction of the gravity, when the tray is lying horizontally.

The hinged frame 1620 is coupled to the base member 1610 via one or more hinge 1624. The hinged frame 1620 is capable to rotate to an opened position or a closed position. The hinged frame includes a horizontal push bar 1622 configured to apply a downward force to the cartridge holder and test cartridges when the hinged frame 1620 is in the closed position. A combination of the slots 1612 and the horizontal push bar 1622 secures the cartridge holder in the tray when the hinged frame 1620 is in the closed position.

The locking mechanism 1630 is to lock the hinged frame 1620 in the closed position when the hinged frame 1620 rotates to the closed position. In an embodiment illustrated in FIG. 1, the lock mechanism 130 includes a spring-loaded pin to reversibly lock the hinged frame 1630 in the closed position when the hinged frame 1630 rotates to the closed position. The lock mechanism 1630 can further include two such spring-loaded pins to lock both left and right side of the hinged frame 1630. The outward ends of the spring-loaded pins can have tilted slope surface so that the hinged frame 1620 can be rotated into the closed position passing the tilted slope surface. When the hinged frame 1620 contacts the tilted slope surface, the spring-loaded pins retract. After the hinged frame 1620 reaching the closed position, the spring-loaded pins return to the extruded positions to lock the hinged frame 1620 in the closed position.

The cartridge tray 1600 can further include a release mechanism 1640 to unlock the hinged frame 1620 from the closed position. The release mechanism 1640 can include two tabs for releasing the test cartridges by a finger motion. The release mechanism 1640 can unlock the hinged frame from the closed position by applying a force to the tabs 1640 to retract the spring-loaded pin so that the test cartridges can be disposed. When a user uses fingers to squeeze the tabs 1640, the spring-loaded pins retract, the hinged frame 1630 can be freely rotates to the opened position. In some embodiments, after the tabs 1640 is squeezed, the spring-loaded pins stay in retracted positions, even that squeezing forces no longer apply to the tabs 1640. Then the hinged frame can be moved to an opened position without any obstacles. Once the tabs 1640 is squeezed again, the spring-loaded pins move back to the extruded position such that the hinged frame can be locked into the closed position again.

Figure 17:
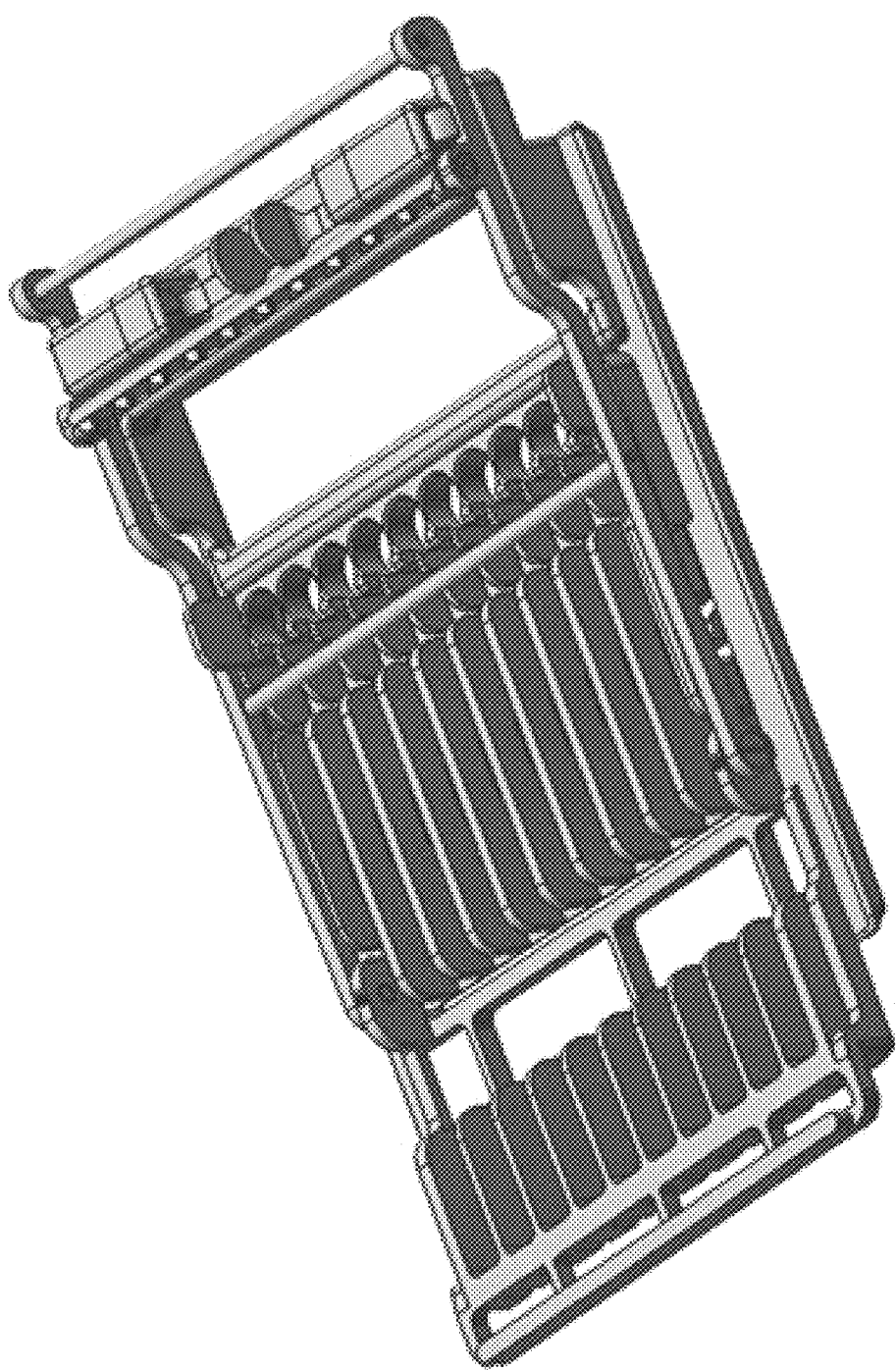
FIG. 17 illustrates an example of a cartridge holder secured in a cartridge tray.

The base member 1610 can further include a holder bar 1670 to help secure the position of the cartridge holder. As shown in FIG. 10, the cartridge holder includes a notch 1001 at the bottom. The notch 1001 is shaped to accommodate the holder bar 1670. In other words, at least some surface of a bottom notch of the cartridge holder is contacting the holder bar such that the cartridge holder does not move laterally relative to the base member, when the cartridge holder is reversibly attached to the base member. FIG. 17 illustrates a cartridge holder secured in a cartridge tray. The cartridge holder cannot move laterally relative to the cartridge tray when the hinged frame is in a closed position, because the bar 1570 is placed in the notch of the cartridge holder.

Figure 18:
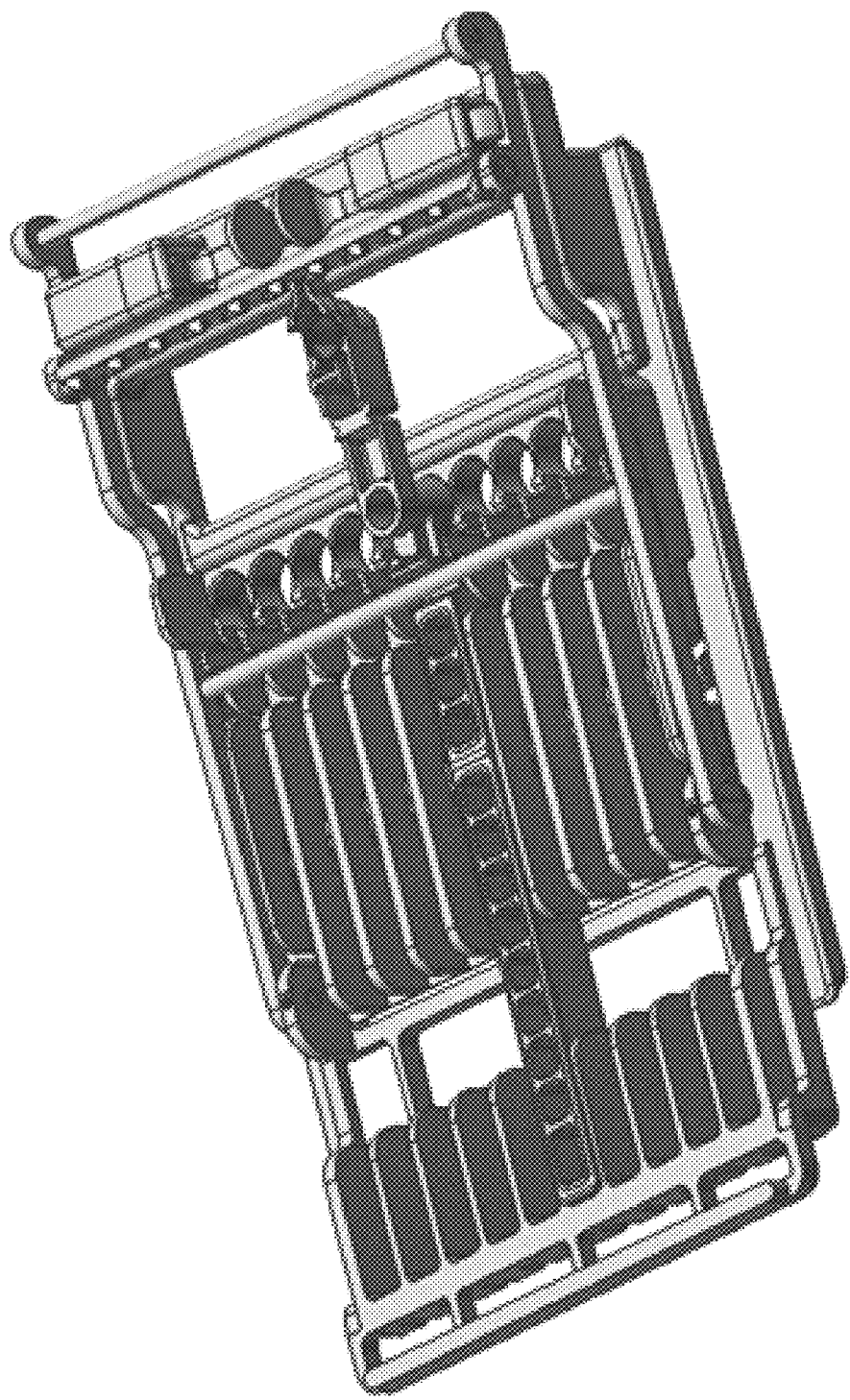
FIG. 18 illustrates an example of a cartridge tray securing a cartridge holder, where the cartridge holder holds a test cartridge with its cap opened.
Figure 19:
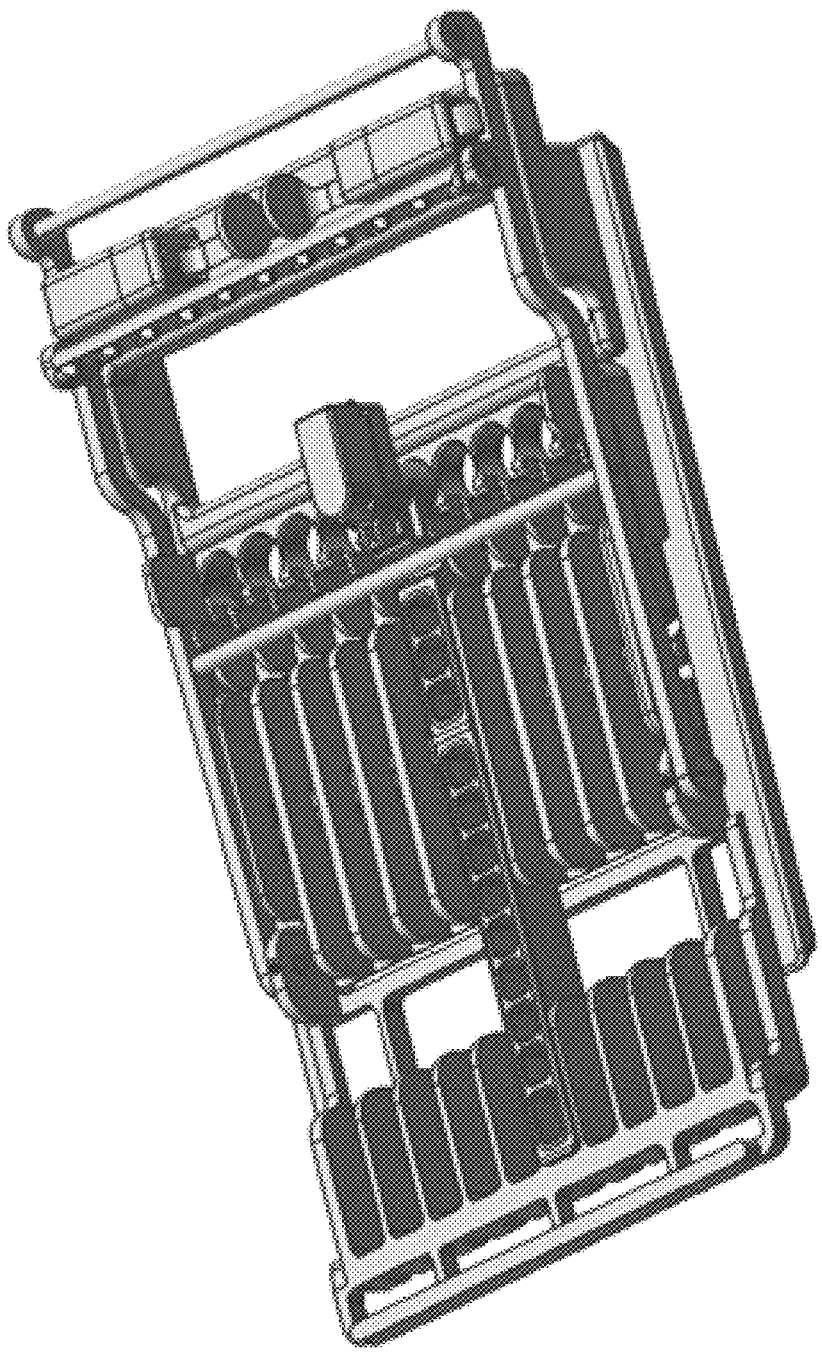
FIG. 19 illustrates an example of a cartridge tray securing a cartridge holder, where the cartridge holder holds a test cartridge with its cap closed.
Figure 20:
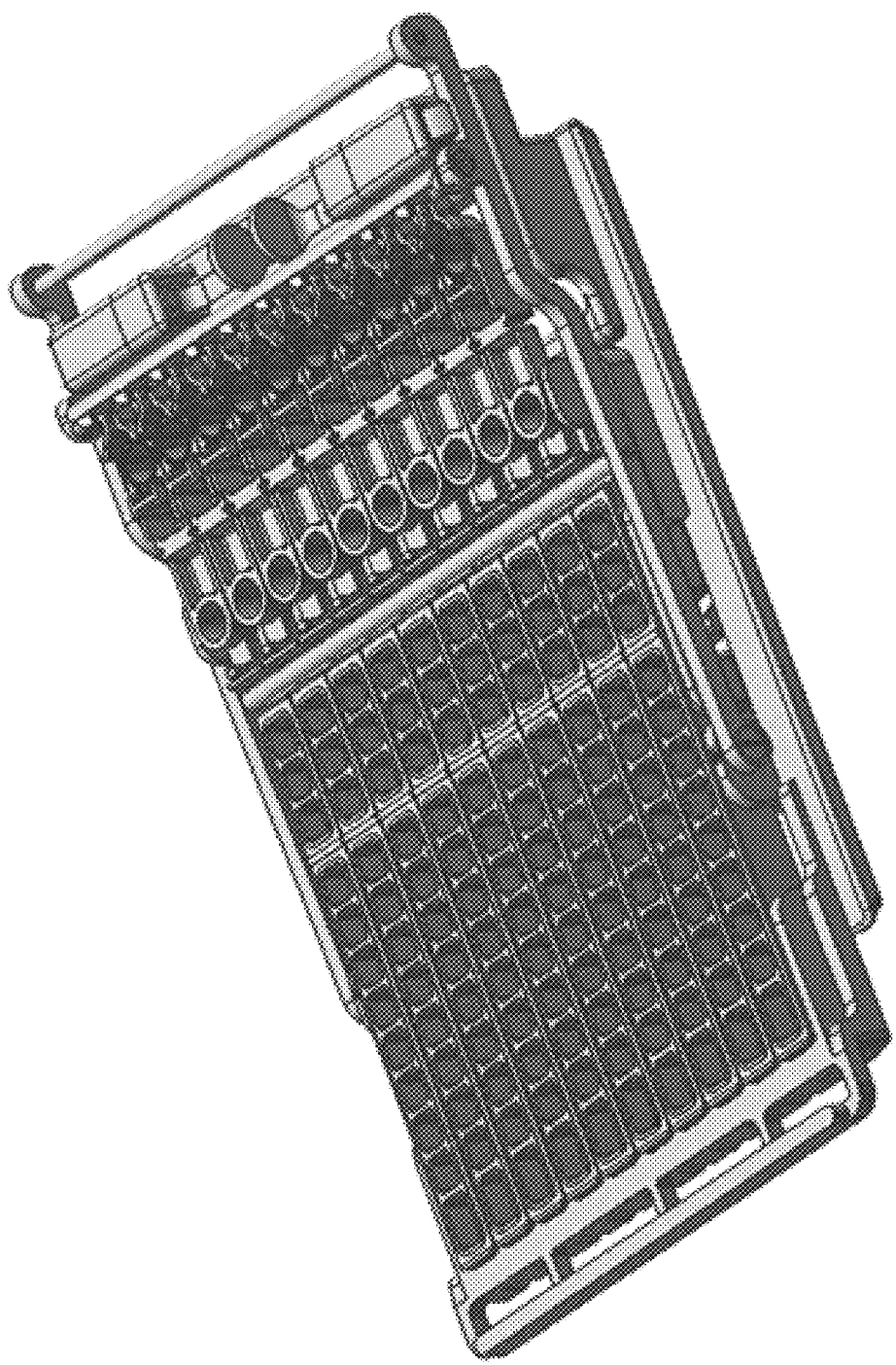
FIG. 20 illustrates an example of a cartridge tray securing a cartridge holder, where the cartridge holder holds multiple test cartridges with their caps opened.
Figure 21:
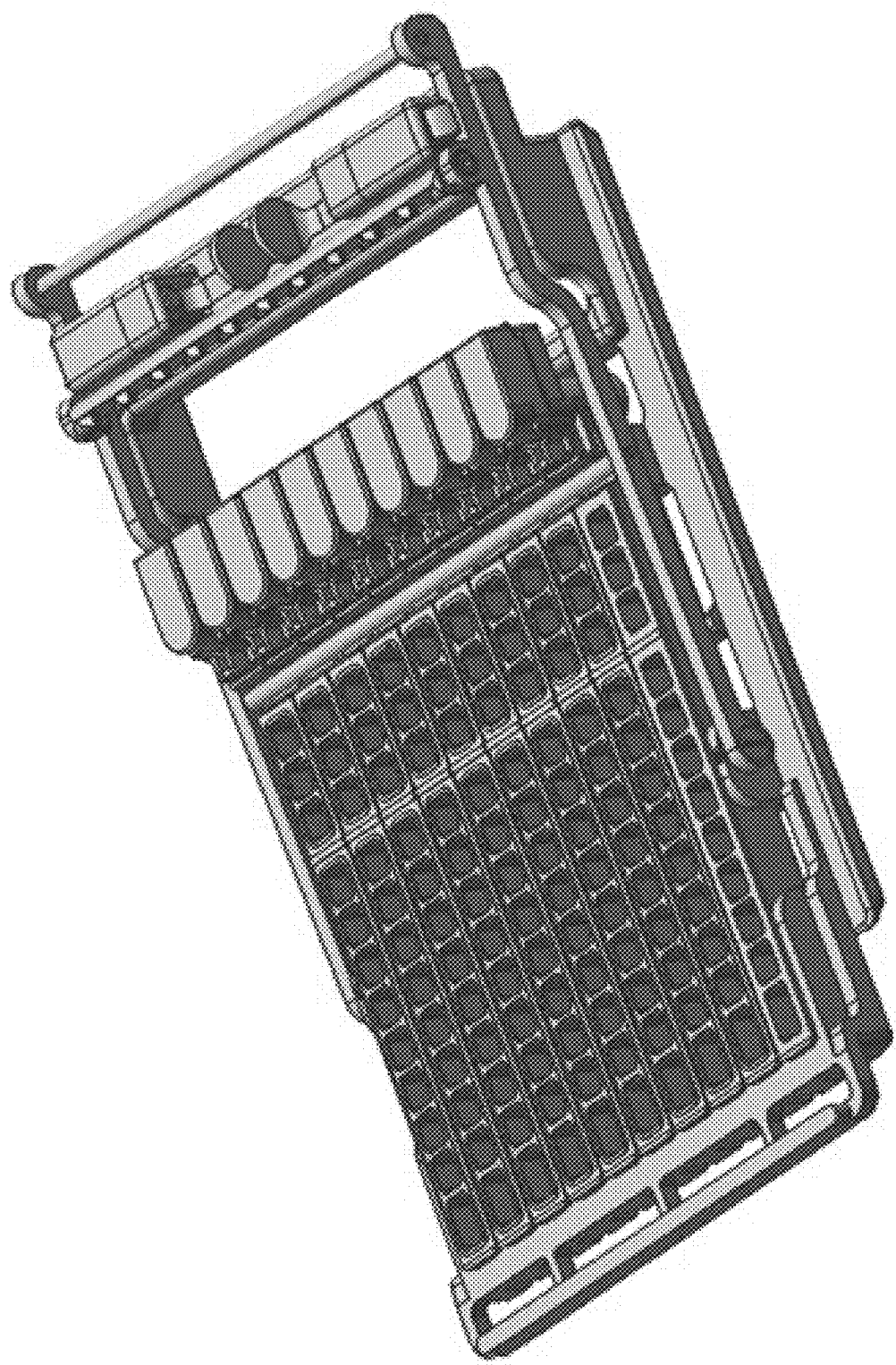
FIG. 21 illustrates an example of a cartridge tray securing a cartridge holder, where the cartridge holder holds multiple test cartridges with their caps closed.

One or more test cartridges can be placed into the cartridge holder. Then the cartridge holder can be placed into the cartridge tray. FIG. 18 illustrates a cartridge tray securing a cartridge holder, where the cartridge holder holds a test cartridge with its cap opened. The tabs of the cartridge tray helps to secure the cap of the test cartridge in its opened position. After conducting a biochemical test, the test apparatus can release the cap from the locked position by squeezing the outward extrusions of the test cartridge and close the cap. FIG. 19 illustrates a cartridge tray securing a cartridge holder, where the cartridge holder holds a test cartridge with its cap closed. Similarly, FIG. 20 illustrates a cartridge tray securing a cartridge holder, where the cartridge holder holds multiple test cartridges with their caps opened. FIG. 21 illustrates a cartridge tray securing a cartridge holder, where the cartridge holder holds multiple test cartridges with their caps closed.

Biochemical Test Using the Cartridge Tray

Figure 22:
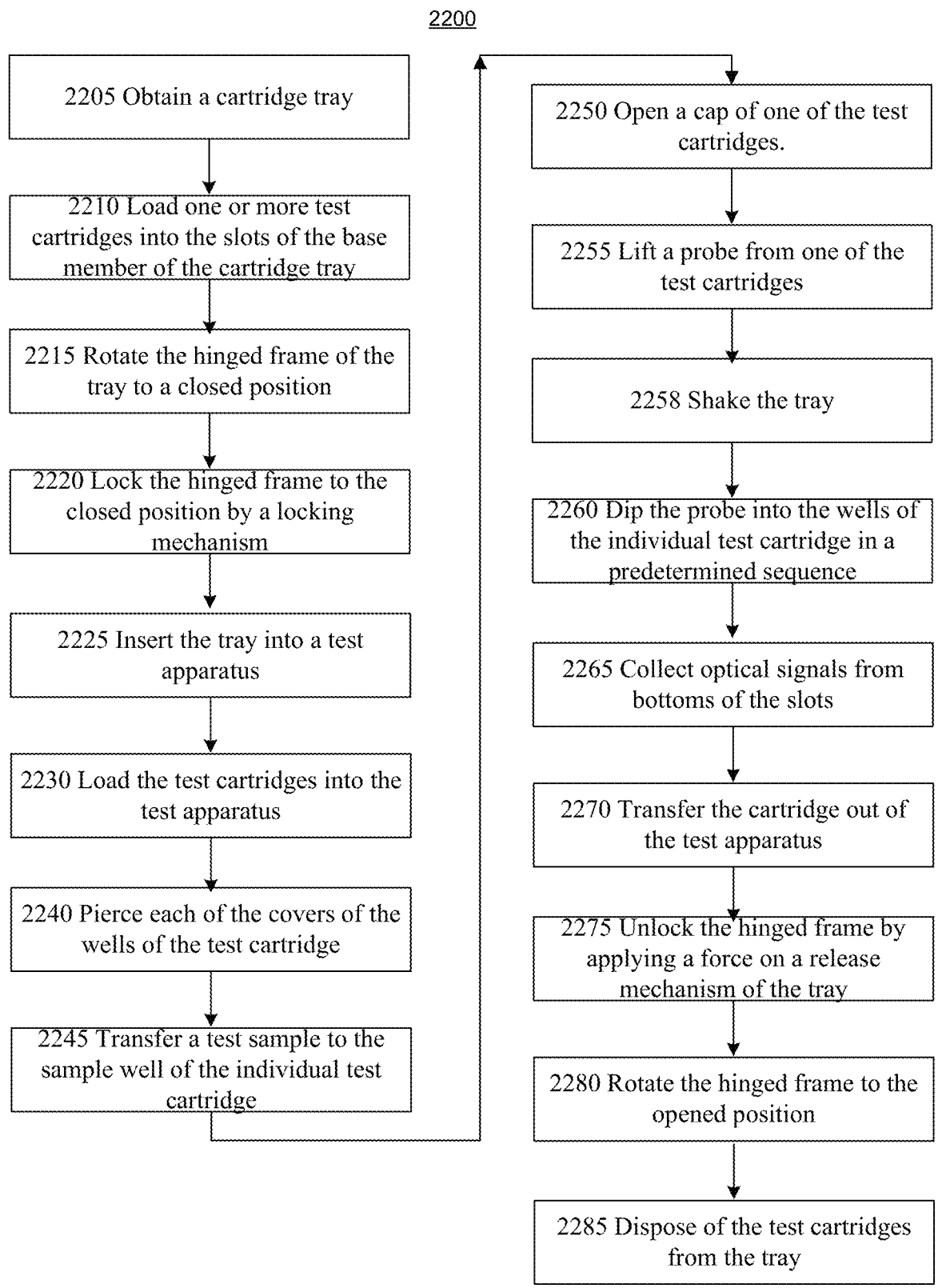
FIG. 22 illustrates an example of a process using a cartridge tray to perform a biochemical test, such as an immunoassay test

FIG. 22 illustrates a sample process 2200 of using a cartridge tray to perform a biochemical test, such as an immunoassay test. At step 2205 of the process 2200, the process obtains a cartridge tray such as the tray 100 illustrated in FIG. 1 or the tray 1600 illustrates in FIG. 16. At step 2210, the process loads one or more test cartridges into the slots of the base member of the cartridge tray. The slots fix the test cartridges from lateral movement in the slots. If a cartridge holder is used (e.g., holder 1000 illustrated in FIG. 10), the process loads the one or more test cartridges into the slots of the cartridge holder. Then the cartridge holder is loaded onto the cartridge tray.

The test cartridges can be secured in the tray as an assembly. At step 2215, the process rotates the hinged frame of the tray to a closed position. At the closed position, the horizontal push bar applies the downward force to the test cartridges to fix the cartridges in the slots. At step 2220, the process locks the hinged frame to the closed position by a locking mechanism of the tray, such as the spring-loaded pins 132 in FIG. 1. At step 2225, the process inserts the tray into a test apparatus.

The test apparatus conduct biochemical tests on the assembly of cartridges secured in the tray. At step 2230, the test apparatus loads the test cartridges into the test apparatus by, e.g., dragging the tray via the handle 114. At step 2240, optionally, the test apparatus pierces each of the covers of the sample well, the reagent wells, the wash wells and the measurement well of the test cartridge secured in the tray. The piecing may be conducted using a dedicated piecing device, using a pipette tip, or using the probe from the cartridge. In some embodiments, the test apparatus can pierce or open the covers of all or some of the test cartridges on the tray at once before conducting the biochemical tests. In some other embodiments, the test apparatus can pierce or open the covers of each test cartridge immediately before conducting the biochemical test on that test cartridge.

At step 2245, the apparatus transfers a test sample to the sample well of the individual test cartridge. At step 2250, the apparatus opens at least one cap of one of the test cartridges. In some embodiments, the test apparatus can open the caps of all or some of the test cartridges on the tray at once before listing any probe from the test cartridges. In some other embodiments, the test apparatus can open the cap of each test cartridge immediately before lifting a probe of that test cartridge.

At step 2255, the test apparatus lifts a probe from one of the test cartridges. At step 2238, optionally, the test apparatus shakes the tray. At step 2260, the test apparatus dips the probe into the sample well, the reagent wells, the wash wells and the measurement well of the individual test cartridge in a predetermined sequence. At step 2265, optionally the test apparatus stops shaking the tray and collects optical signals from, e.g., bottoms of the slots when optical signals can travel through transparent windows of the cartridges and the bottoms of the slots.

After conducting the biochemical tests, the tray can be released from the test apparatus and the cartridges can be removed from the tray. At step 2270, after the measurement, if the test apparatus has stopped shaking the tray at step 2265, then it transfers the cartridge out of the test apparatus; otherwise, stop shaking before transferring the cartridge out of the test apparatus. At step 2275, the process unlocks the hinged frame by applying a force on a release mechanism of the tray. At step 2280, the process rotates the hinged frame to the opened position. At step 2285, the process disposes of the test cartridges from the tray.

Those skilled in the art will appreciate that the logic illustrated in FIG. 22 and described above, and in each of the flow diagrams discussed below, may be altered in a variety of ways. For example, the order of the logic may be rearranged, substeps may be performed in parallel, other logic may be included, etc.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. An assembly comprising:
   a tray that includes
      a base member that includes a first plurality of horizontally elongated slots arranged adjacent to one another, and
      a frame configured to rotate about a hinge connected to the base member between an opened position and a closed position in which the frame extends across the first plurality of horizontally elongated slots; and
   a cartridge holder that includes a second plurality of horizontally elongated slots configured to receive test cartridges,
      wherein when the cartridge holder is inserted into the tray, the second plurality of horizontally elongated slots substantially aligns with the first plurality of horizontally elongated slots.

2. The assembly of claim 1,
   wherein the frame includes a horizontal push bar that extends across the first plurality of horizontally elongated slots of the base member, and
   wherein when the frame is rotated to the closed position, the horizontal push bar applies a downward force to test cartridges loaded in the second plurality of horizontally elongated slots in the cartridge holder.

3. The assembly of claim 1,
  wherein the cartridge holder further includes a notch disposed along a bottom surface, and
  wherein when the cartridge holder is inserted into the tray, the notch is aligned with a holder bar of the tray to prevent lateral movement.

4. The assembly of claim 1, wherein the tray further includes a locking mechanism configured to lock the frame when the frame is rotated to the closed position.

5. The assembly of claim 4, wherein the tray further includes a release mechanism configured to unlock the frame from the closed position.

6. The assembly of claim 1, wherein the hinge is one of a pair of hinges connected to the base member along opposing sides.

7. The assembly of claim 1, wherein the first plurality of horizontally elongated slots in the base member of the tray are only partially enclosed.

8. The assembly of claim 1, wherein the second plurality of horizontally elongated slots in the cartridge holder are only partially enclosed.

9. A method for loading a plurality of test cartridges into a test apparatus, the method comprising:
  acquiring the assembly of claim 1;
  loading the plurality of test cartridges into the second plurality of horizontally elongated slots in the cartridge holder;
  inserting the cartridge holder into the tray by aligning the second plurality of horizontally elongated slots with the first plurality of horizontally elongated slots;
  rotating the frame of the tray to the closed position; and
  inserting the assembly into the test apparatus.

10. The assembly of claim 1, wherein the hinge allows a limited angle of rotation between the base member and the frame.

11. The assembly of claim 1, wherein each of the first plurality of horizontally elongated slots has a top opening designed to receive a test cartridge, and wherein a width of the top opening fits the test cartridge to prevent lateral movement.

12. The assembly of claim 1, wherein each of the first plurality of horizontally elongated slots has a bottom opening that permits light to be projected therethrough toward a light-transmissive bottom of a well of a test cartridge.

13. The assembly of claim 1, wherein each test cartridge includes a protective cap that encloses a portion of a probe extending above a well, and wherein the tray further comprises:
  a plurality of tabs aligned with the first plurality of horizontally elongated slots in the base member,
    wherein each tab is configured to secure the protective cap of a corresponding test cartridge to prevent the protective cap from reverting back when opened.

14. The assembly of claim 1, wherein each of the first plurality of horizontally elongated slots has a substantially rectangular shape that is only partially enclosed.

15. The assembly of claim 1,
  wherein the base member has a pair of longitudinal sides that extend parallel to the first plurality of horizontally elongated slots, and
  wherein each longitudinal side includes a structural feature to facilitate positioning of the tray with respect to a test apparatus.

* * * * *